(12) United States Patent
Bach et al.

(10) Patent No.: US 9,206,351 B2
(45) Date of Patent: Dec. 8, 2015

(54) MATERIALS FOR ORGANIC ELECTROLUMINESCENT DEVICES

(75) Inventors: Ingrid Bach, Hofheim (DE); Arne Buesing, Frankfurt am Main (DE); Susanne Heun, Bad Soden (DE); Philipp Stoessel, Frankfurt am Main (DE); Michael Holbach, Langen (DE); Jonas Kroeber, Frankfurt (DE); Amir Hossain Parham, Frankfurt (DE)

(73) Assignee: Merck Patent GmbH, Darmstadt (DE)

( * ) Notice: Subject to any disclaimer, the term of this patent is extended or adjusted under 35 U.S.C. 154(b) by 1493 days.

(21) Appl. No.: 12/302,560

(22) PCT Filed: May 21, 2007

(86) PCT No.: PCT/EP2007/004499
§ 371 (c)(1),
(2), (4) Date: Nov. 26, 2008

(87) PCT Pub. No.: WO2007/137725
PCT Pub. Date: Dec. 6, 2007

(65) Prior Publication Data
US 2009/0167166 A1  Jul. 2, 2009

(30) Foreign Application Priority Data

May 31, 2006 (DE) .......................... 10 2006 025 777

(51) Int. Cl.
| | |
|---|---|
| *C09K 11/06* | (2006.01) |
| *H01L 51/00* | (2006.01) |
| *C07C 225/22* | (2006.01) |
| *C07F 9/53* | (2006.01) |
| *C09B 17/00* | (2006.01) |
| *C09B 19/00* | (2006.01) |
| *C09B 21/00* | (2006.01) |
| *C09B 57/00* | (2006.01) |
| *H01L 51/50* | (2006.01) |

(52) U.S. Cl.
CPC .............. *C09K 11/06* (2013.01); *C07C 225/22* (2013.01); *C07F 9/5325* (2013.01); *C09B 17/00* (2013.01); *C09B 19/00* (2013.01); *C09B 21/00* (2013.01); *C09B 57/00* (2013.01); *C09B 57/007* (2013.01); *C09B 57/008* (2013.01); *H01L 51/0059* (2013.01); *H01L 51/0079* (2013.01); *C09K 2211/1014* (2013.01); *C09K 2211/1018* (2013.01); *H01L 51/5016* (2013.01)

(58) Field of Classification Search
CPC ............ C07F 7/10; C07F 9/02; C07F 9/5325; C07C 221/00; C07C 225/16; C07C 225/18; C07C 225/22; C07D 251/12; C07D 403/08; C07D 401/04; C07D 413/08; C07D 417/10; H01L 51/0059; H01L 51/0079; C09K 11/06; C09K 2211/1014; C09K 2211/1018
See application file for complete search history.

(56) References Cited

U.S. PATENT DOCUMENTS

| | | | | |
|---|---|---|---|---|
| 5,378,519 | A | * | 1/1995 | Kikuchi et al. ................ 428/690 |
| 5,484,922 | A | * | 1/1996 | Moore et al. ...................... 546/7 |
| 5,639,914 | A | * | 6/1997 | Tomiyama et al. ............ 564/309 |
| 6,280,859 | B1 | * | 8/2001 | Onikubo et al. ............... 428/690 |
| 6,458,475 | B1 | * | 10/2002 | Adachi et al. ................. 428/690 |
| 7,345,301 | B2 | | 3/2008 | Gerhard et al. |
| 2007/0099026 | A1 | | 5/2007 | Lee et al. |
| 2008/0145699 | A1 | | 6/2008 | Yabe et al. |

FOREIGN PATENT DOCUMENTS

| | | |
|---|---|---|
| EP | 1489154 A1 | 12/2004 |
| JP | 2003515897 A | 5/2003 |
| JP | 2003-267976 A | 9/2003 |
| JP | 2005-154396 A | 6/2005 |
| JP | 2005158289 A | 6/2005 |
| JP | 2005255986 A | 9/2005 |
| JP | 2006199679 A | 8/2006 |
| JP | 2007027092 A | 2/2007 |
| WO | WO-01/41512 A1 | 6/2001 |
| WO | WO-2004/093207 A2 | 10/2004 |
| WO | WO-2005082851 A2 | 9/2005 |

OTHER PUBLICATIONS

English Language machine translation of JP 2005-255986 A, part 1, 2005.*
English Language machine translation of JP 2005-255986 A, part 2, 2005.*
Kapturkiewicz, A., et al., "Properties of the Intramolecular Excited Charge-Transfer States of Carbazol-9-yl Derivatives of Aromatic Ketones", J. Phys. Cem., vol. 103, (1999) pp. 8145-8155.

* cited by examiner

*Primary Examiner* — Michael H Wilson
(74) *Attorney, Agent, or Firm* — Drinker Biddle & Reath LLP

(57) ABSTRACT

The present invention relates to compounds according to formula (1) and/or according to formulae (4) to (10) and their use in organic electroluminescent devices, in particular as a matrix material in phosphorescent devices.

18 Claims, No Drawings

MATERIALS FOR ORGANIC ELECTROLUMINESCENT DEVICES

RELATED APPLICATIONS

This application is a national stage application (under 35 U.S.C. §371) of PCT/EP2007/004499, filed May 21, 2007, which claims benefit of German Application No. 10 2006 025 777.4, filed May 31, 2006.

Organic semiconductors are being developed for a number of different applications which can be ascribed to the electronics industry in the broadest sense. The structure of organic electroluminescent devices (OLEDs) in which these organic semiconductors are employed as functional materials is described, for example, in U.S. Pat. No. 4,539,507, U.S. Pat. No. 5,151,629, EP 0676461 and WO 98/27136.

A development which has been evident in recent years is the use of organometallic complexes which exhibit phosphorescence instead of fluorescence (M. A. Baldo et al., *Appl Phys. Lett.* 1999, 75, 4-6). For quantum-mechanical reasons, an up to four-fold increase in energy and power efficiency is possible using organometallic compounds as phosphorescence emitters. Whether this development will succeed depends on whether corresponding device compositions are found which are also able to implement these advantages (triplet emission=phosphorescence compared with singlet emission=fluorescence) in the OLEDs.

In general, there are still considerable problems in OLEDs which exhibit triplet emission. Thus, the operating lifetime is generally still too short, which has hitherto prevented the introduction of phosphorescent OLEDs in high-quality and long-lived devices. Furthermore, the charge balance in phosphorescent devices comprising the matrix materials in accordance with the prior art has not yet been levelled out. This results in higher voltages and consequently lower efficiency and shorter lifetimes. Furthermore, many of the matrix materials in accordance with the prior art do not have adequately high solubility, and these materials are consequently not suitable for processing from solution.

In phosphorescent OLEDs, the matrix material used is frequently 4,4'-bis(N-carbazolyl)biphenyl (CBP). The disadvantages are short lifetimes of the devices produced therewith and high operating voltages, which result in low power efficiencies. In addition, CBP has an inadequately high glass transition temperature. Furthermore, it has been found that CBP is unsuitable for blue-emitting electroluminescent devices, which results in poor efficiency. In addition, the construction of devices comprising CBP is complex since a hole-blocking layer and an electron-transport layer additionally have to be used.

Improved triplet matrix materials, based on keto compounds and phosphine oxide compounds, are described in WO 04/093207 and in WO 05/003253. However, the charge balance in the device is still unsatisfactory with the matrix materials described therein since these compounds transport exclusively electrons owing to their low HOMOs.

JP 2005/154396, besides further carbazole derivatives, also mentions 4,4'-bis(N,N'-carbazolyl)benzophenone as triplet matrix material. These compounds exhibit disadvantages due to the direct conjugation between the carbazole group and the carbonyl unit, which results in charge-transfer complexes.

Surprisingly, it has been found that bipolar compounds in which at least one aromatic carbonyl and/or at least one phosphine oxide is linked to at least one carbazole and/or at least one substituted arylamine exhibit improvements compared with the above-mentioned prior art in particular if a conjugation interruption is present between these groups. These materials furthermore have the advantage that they are very readily soluble in common organic solvents. They are therefore also suitable for the production of organic electronic devices from solution. In addition, the materials exhibit very good film-formation properties on processing from solution. The present invention therefore relates to these materials and to the use thereof in organic electronic devices.

The invention relates to compounds containing at least one structural element of the formula (1)

Formula (1)

where the following applies to the symbols and indices used:
X is on each occurrence, identically or differently, C, P(Ar) or P(Ar—Y);
Ar is on each occurrence, identically or differently, an aromatic or heteroaromatic ring system having 5 to 60 aromatic ring atoms, which may be substituted by one or more radicals $R^1$;
$R^1$ is on each occurrence, identically or differently, H, F, Cl, Br, I, $N(Ar^1)_2$, CN, $NO_2$, $Si(R^2)_3$, $B(OR^2)_2$, $C(=O)Ar^1$, $P(=O)(Ar^1)_2$, $S(=O)Ar^1$, $S(=O)_2Ar^1$, $CR^2=CR^2(Ar^1)$, tosylate, triflate, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a combination of these systems; two or more substituents $R^1$ here may also form a mono- or polycyclic aliphatic or aromatic ring system with one another;
$Ar^1$ is on each occurrence, identically or differently, an aromatic or heteroaromatic ring system having 5 to 60 aromatic ring atoms, which may be substituted by one or more radicals 2;
$R^2$ is on each occurrence, identically or differently, H, F or an aliphatic, aromatic and/or heteroaromatic hydrocarbon radical having 1 to 20 C atoms, in which, in addition, H atoms may be replaced by F; two or more substituents $R^2$ here may also from a mono- or polycyclic aliphatic or aromatic ring system with one another;
Y is on each occurrence, identically or differently, a group of the formula (2) or formula (3)

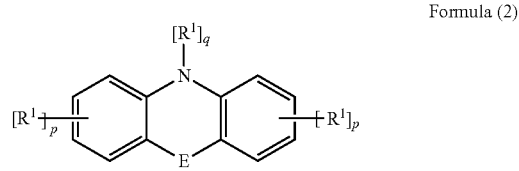

Formula (2)

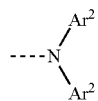
Formula (3)

where the unit of the formula (2) is linked to Ar via any desired position, preferably via N, and the unit of the formula (3) is linked to Ar via N, where R¹ has the above-mentioned meaning and furthermore:

E stands for O, S, N(R¹), P(R¹), P(=O)R¹, C(R¹)₂, Si(R¹)₂ or a single bond;

Ar² is, identically or differently on each occurrence, an aryl or heteroaryl group having 5 to 20 aromatic ring atoms or a triarylamine group having 15 to 30 aromatic ring atoms, each of which may be substituted by one or more radicals R¹, with the proviso that at least one substituent R¹ which stands for an alkyl or silyl group is present on at least one group Ar²;

p is on each occurrence, identically or differently, 0, 1, 2, 3 or 4;

q is 0 or 1, where q 0 if the unit of the formula (2) is bonded to Ar¹ via the nitrogen, and q=1 if the unit of the formula (2) is bonded to Ar¹ via an atom other than the nitrogen;

with the proviso that the group Ar which is bonded to X and to Y is not continuously conjugated if the compound of the formula (1) has precisely one carbonyl function;

with the exception of the following compound:

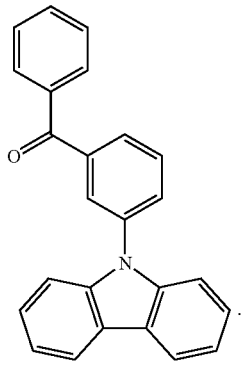 [SMILES: O=C(c1ccccc1)c1cccc(-n2c3ccccc3c3ccccc32)c1]

Although evident from the structure depicted above, it should explicitly be emphasised here that the compounds according to the invention may also contain a plurality of groups X=O, i.e. a plurality of carbonyl and/or phosphine oxide groups, or also a plurality of groups Y.

Preference is given to compounds according to the invention which contain at least two groups X=O, i.e. at least two carbonyl and/or phosphine oxide groups, and/or at least two groups Y.

In a further preferred embodiment of the invention, the ratio of groups X=O to groups Y is between 1:10 and 10:1, particularly preferably between 1:5 and 5:1, in particular between 1:3 and 3:1.

The compounds according to the invention preferably have a glass transition temperature $T_G$ of greater than 70° C., particularly preferably greater than 100° C., very particularly preferably greater than 130° C.

For the purposes of this invention, an aryl group contains 6 to 40 C atoms; for the purposes of this invention, a heteroaryl group contains 2 to 40 C atoms and at least 1 heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

For the purposes of this invention, an aromatic ring system contains 6 to 40 C atoms in the ring system. For the purposes of this invention, a heteroaromatic ring system contains 2 to 40 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is to be taken to mean a system which does not necessarily contain only aryl or heteroaryl groups, but instead in which a plurality of aryl or heteroaryl groups may also be interrupted by a non-aromatic unit (preferably less than 10% of the atoms other than H), such as, for example, an sp³-hybridised C, N or O atom. Thus, for example, systems such as 9,9'-spirobifluorene, 9,9-diaryifluorene, triarylamine, diaryl ether, stilbene, etc. are also to be regarded as aromatic ring systems for the purposes of this invention, likewise systems in which two or more aryl groups are interrupted, for example, by a linear or cyclic alkyl group or by a silyl group.

For the purposes of this invention, an aromatic ring system which is not continuously conjugated is taken to mean an aromatic ring system, as described above, in which a plurality of aryl or heteroaryl groups are interrupted by a non-conjugated unit, for example an sp³-hybridised carbon atom. An aromatic ring system which is not continuously conjugated is furthermore taken to mean an aryl or heteroaryl group which is linked via an odd number of carbon atoms, such as, for example, meta-phenylene or 2,6-linked pyridine, or an aromatic or heteroaromatic ring system which contains at least one aryl or heteroaryl group of this type, since continuous conjugation is impossible via these positions.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-40 aromatic ring atoms, which may also in each case be substituted by the above-mentioned radicals R and which may be linked to the aromatic or heteroaromatic ring system via any desired positions, is taken to mean, in particular, groups derived from benzene, naphthalene, anthracene, phenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preferred structures which contain at least one structural element of the formula (1) are compounds of the formulae (4), (5), (6), (7), (8), (9) and (10)

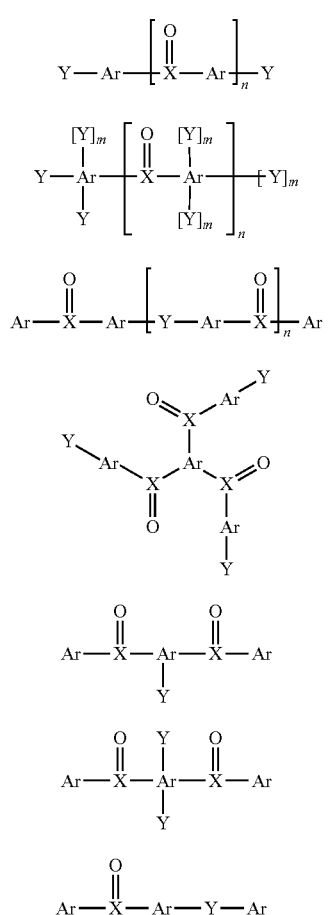

Formula (4)

Formula (5)

Formula (6)

Formula (7)

Formula (8)

Formula (9)

Formula (10)

where the symbols and indices have the meanings indicated above, and furthermore:
m is on each occurrence, identically or differently, 0 or 1;
n is on each occurrence, identically or differently, 1, 2, 3, 4 or 5.

Preference is given to compounds which contain at least one structural element of the formula (1) and compounds of the formulae (4) to (10) in which the group Ar, which is simultaneously bonded to X and to Y, is not continuously conjugated, i.e. in which Ar has a conjugation interruption owing to a non-conjugated unit or an arylene unit which is not continuously conjugated, for example a meta-linked arylene unit, so that X and Y are not in conjugation with one another.

Preferred groups Ar in formula (1) or formulae (4) to (10) only contain phenyl and/or naphthyl groups, but no larger condensed aromatic systems. Preferred groups Ar are therefore aromatic ring systems built up from phenyl and/or naphthyl groups or combinations of these systems, such as, for example, biphenyl, fluorene, spirobifluorene, etc.

Particularly preferred groups Ar which are bonded to X and to Y are selected from the units of the formula (11) to formula (17)

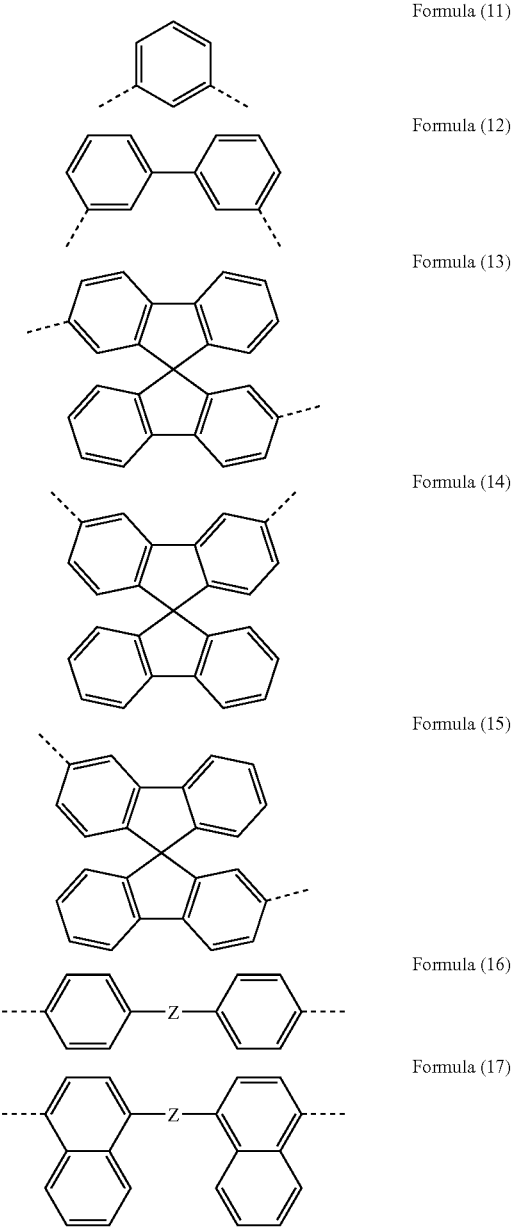

Formula (11)

Formula (12)

Formula (13)

Formula (14)

Formula (15)

Formula (16)

Formula (17)

where the dashed bond in each case indicates the link to X and to Y, where the units may in each case be substituted by one or more radicals $R^1$ and furthermore:

Z is on each occurrence, identically or differently, —[C(R¹)₂]ₖ—, Si(R¹)₂, O or S;
k is 1, 2, 3, 4, 5 or 6.

In the formulae (11) to (17), only one bond to X and to Y is drawn in each case. If the compound according to the invention contains a plurality of units X=O or a plurality of units Y, such as, for example, the compounds of the formula (5) depicted above, the units of the formulae (11) to (17) then of course also have correspondingly more bonds to X or Y.

Preferred units of the formula (2) or formula (3) are the following formulae (2a) and (3a)

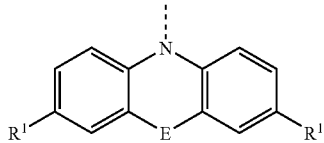

Formula (2a)

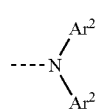

Formula (3a)

where the units are linked to Ar via the nitrogen, where R¹ has the meaning indicated above and furthermore:
E stands for a single bond, O, S or N(R¹);
Ar² is, identically or differently on each occurrence, an aryl or heteroaryl group having 5 to 10 aromatic ring atoms or a triarylamine group having 18 to 24 aromatic ring atoms, each of which may be substituted by one or more radicals R¹, with the proviso that at least one substituent R¹ which stands for an alkyl or silyl group is present on at least one group Ar².

Ar² particularly preferably stands, identically or differently, for phenyl, 1-naphthyl, 2-naphthyl, triphenylamine, naphthyldiphenylamine or dinaphthylphenylamine, where at least one of these groups is substituted by at least one methyl or tert-butyl group or at least one group Si(R³)₃, in which R³ represents an alkyl group having 1 to 4 C atoms.

Preference is furthermore given to compounds containing at least one structural element of the formula (1) and compounds of the formulae (4) to (10) in which the symbol R¹ identically or differently on each occurrence, stands for H, F, Br, N(Ar¹)₂, P(=O)(Ar¹)₂, C(=O)Ar¹, CR²CR²Ar¹, a straight-chain alkyl group having 1 to 5 C atoms or a branched alkyl group having 3 to 5 C atoms, where in each case one or more non-adjacent CH₂ groups may be replaced by —R²C=CR²— or —O— and where one or more H atoms may be replaced by F, or an aryl group having 6 to 16 C atoms or heteroaryl group having 2 to 16 C atoms or a spirobifluorene group, each of which may be substituted by one or more radicals R², or a combination of two or three of these systems. Particularly preferred radicals R¹ are, identically or differently on each occurrence, H, F, Br, methyl, ethyl, isopropyl, tert-butyl, where in each case one or more H atoms may be replaced by F, or a phenyl, naphthyl or spirobifluorenyl group, each of which may be substituted by one or more radicals R², or a combination of two of these systems. On incorporation into polymers, oligomers or dendrimers and in the case of compounds which are processed from solution, linear or branched alkyl chains having up to 10 C atoms are also preferred. Bromine, boronic acid or boronic acid derivatives as substituents are particularly preferred for use of this compound for the preparation of other compounds according to the invention or for use as monomer for the preparation of polymers.

Preference is furthermore given to symmetrical and symmetrically substituted compounds, i.e. compounds in which all symbols X are identical, and compounds in which all symbols Y are identical. The compounds furthermore preferably have a symmetrical structure with respect to the groups Ar. The substituents R¹ are again furthermore preferably selected identically in the structures.

Examples of preferred compounds containing structural elements of the formula (1) are structures (1) to (140) depicted below. These structures may also be substituted by R¹. For reasons of clarity, these possible substituents are in most cases not depicted.

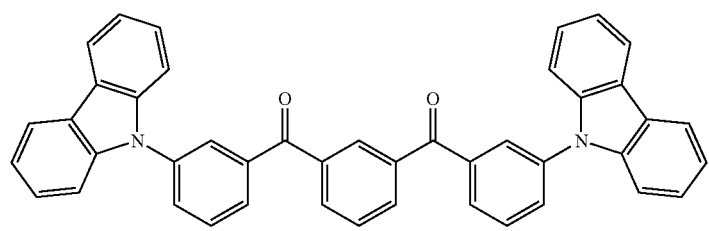

(1)

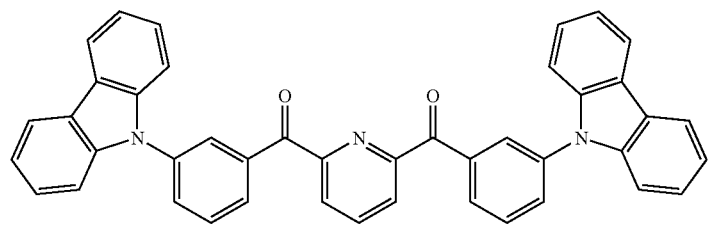

(2)

(3)
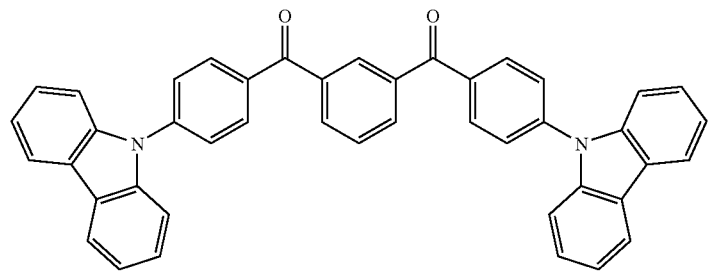
(4)
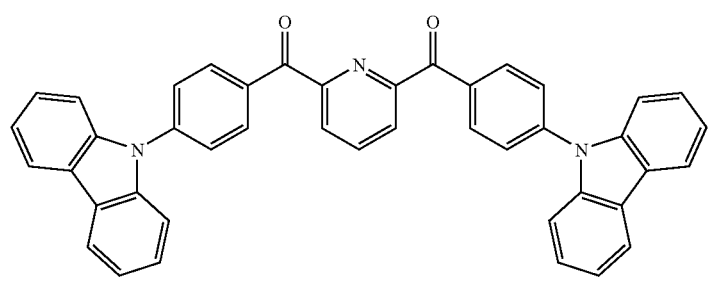
(4)
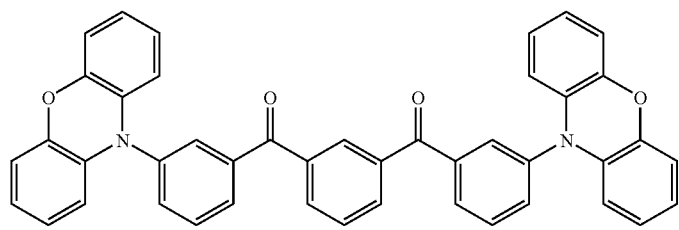
(5)
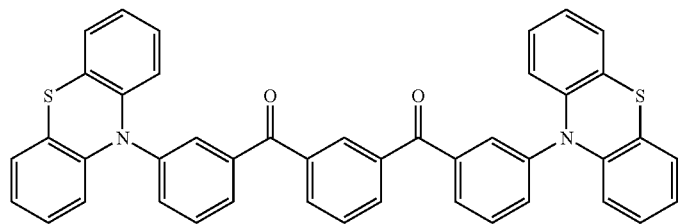
(6)
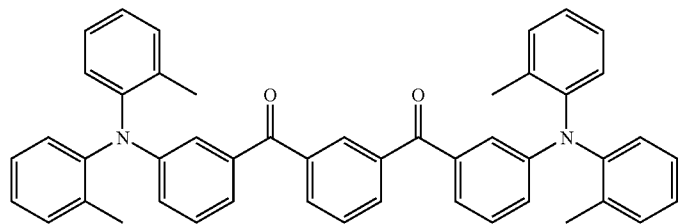
(7)
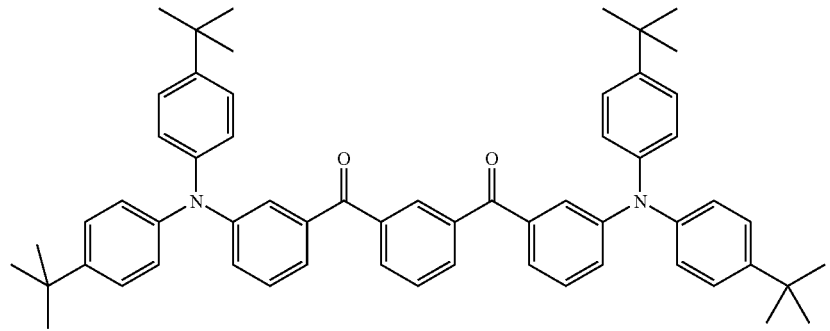

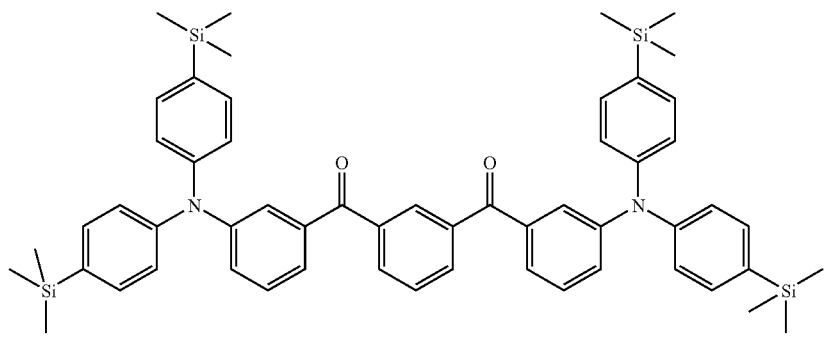
(8)
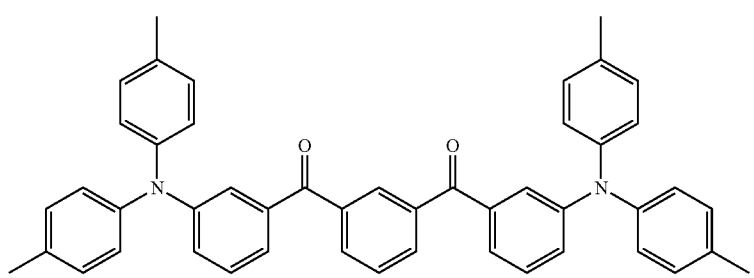
(9)
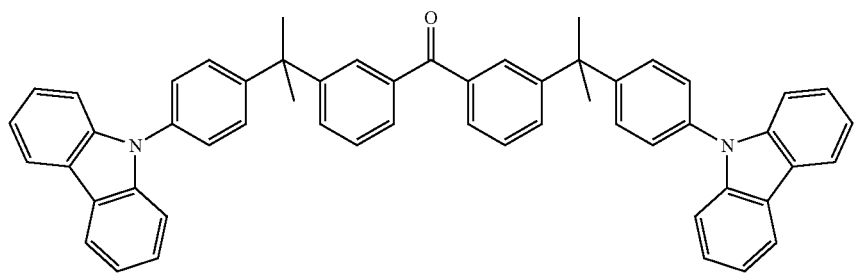
(10)
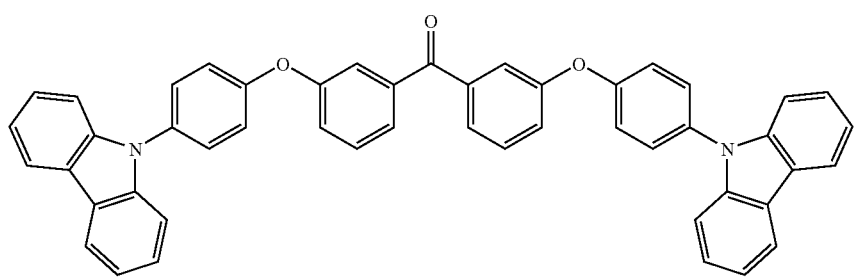
(11)
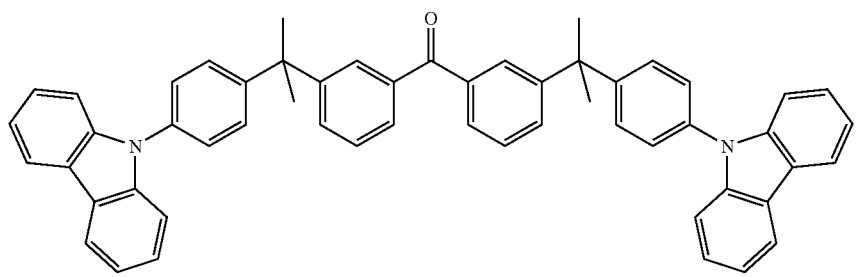
(12)

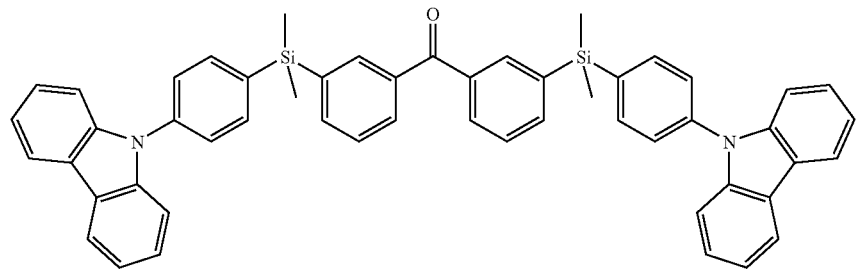
(13)
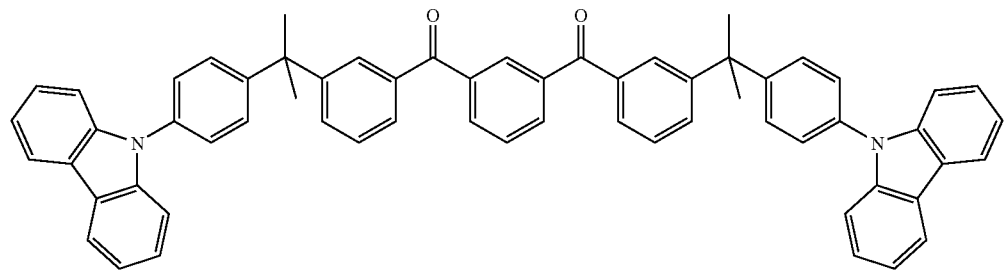
(14)
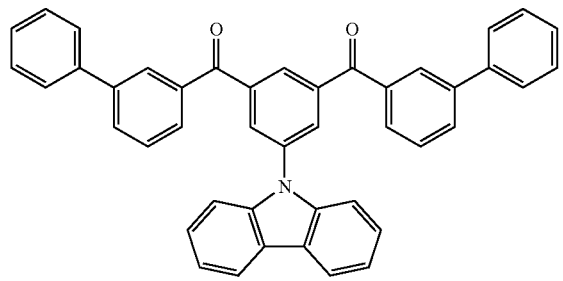
(15)
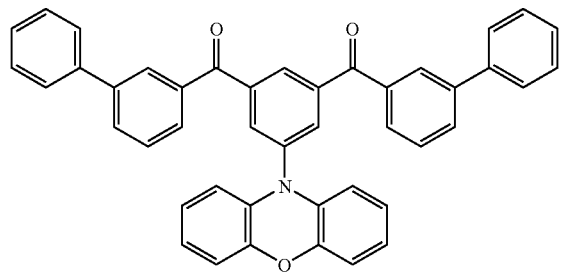
(16)
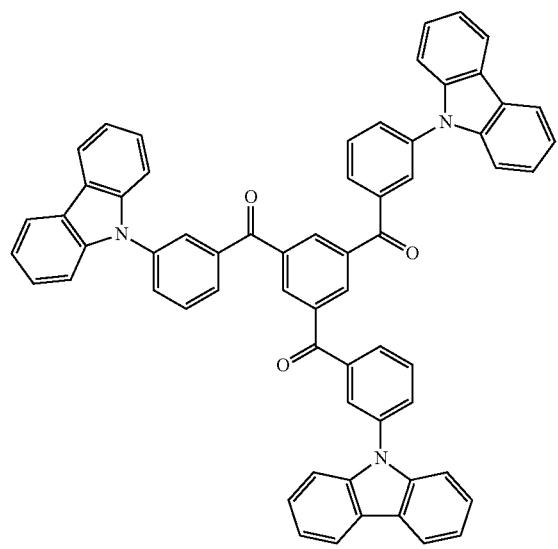
(17)
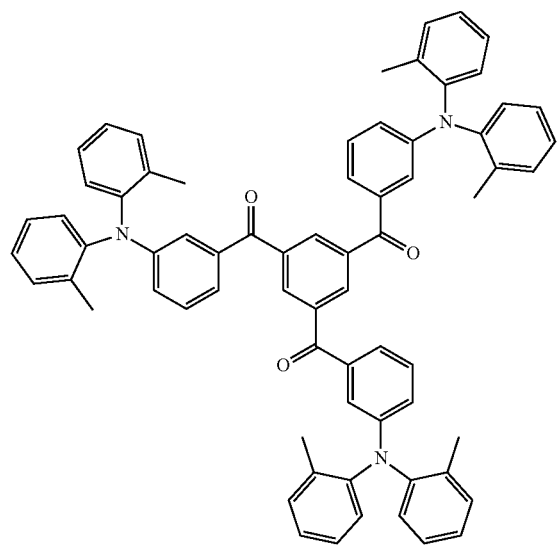
(18)

-continued
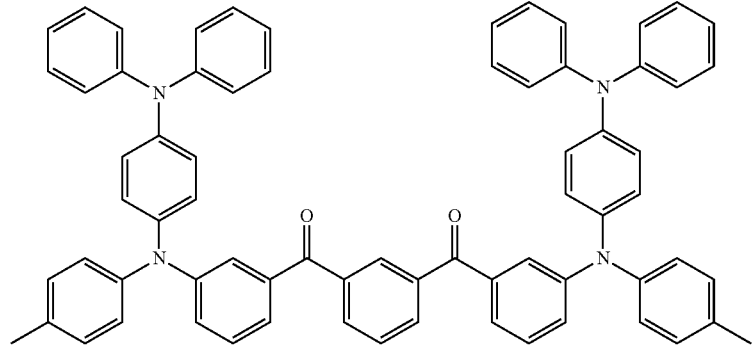
(19)
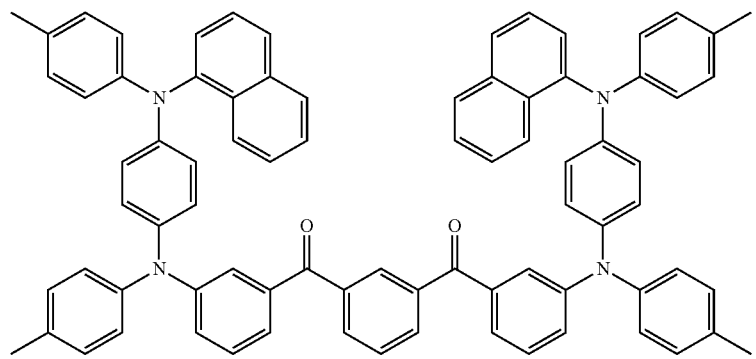
(20)
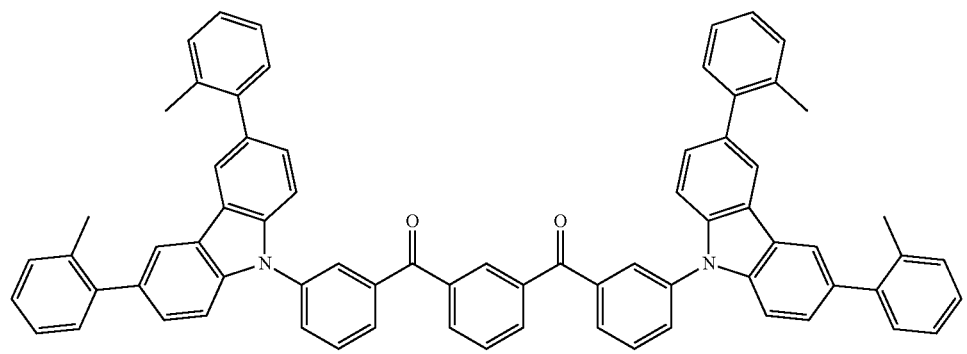
(21)
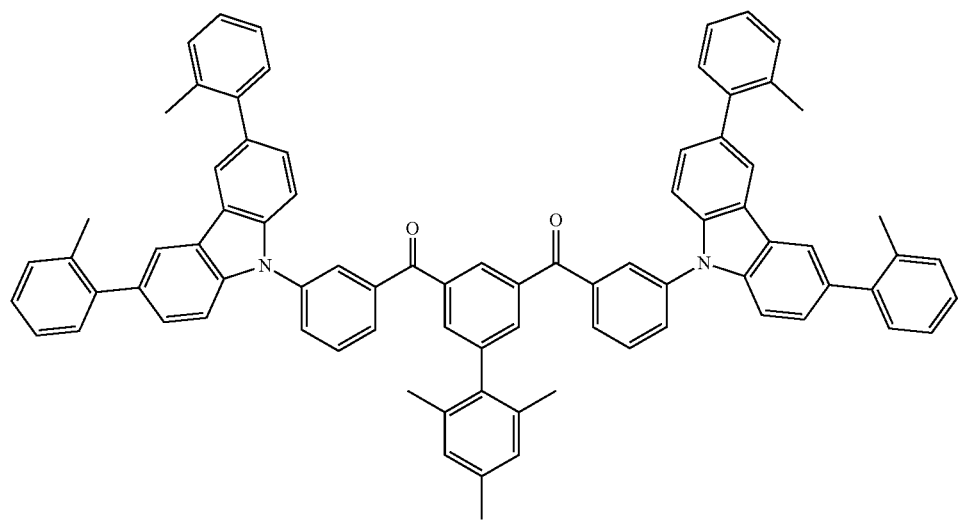
(22)

-continued
(23)
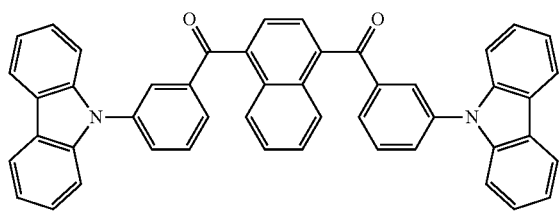
(24)
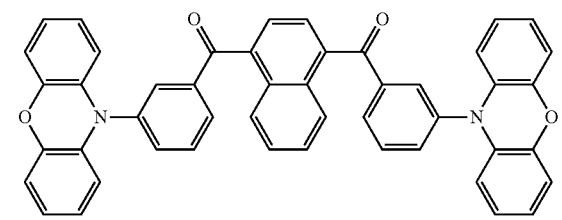
(25)
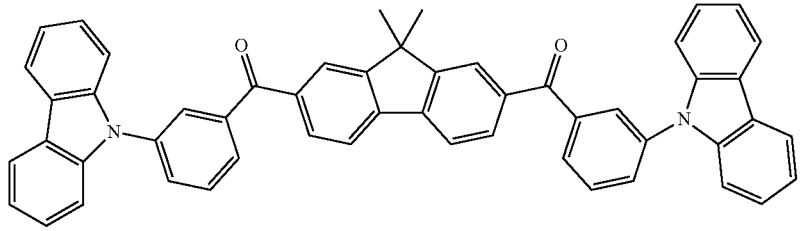
(26)
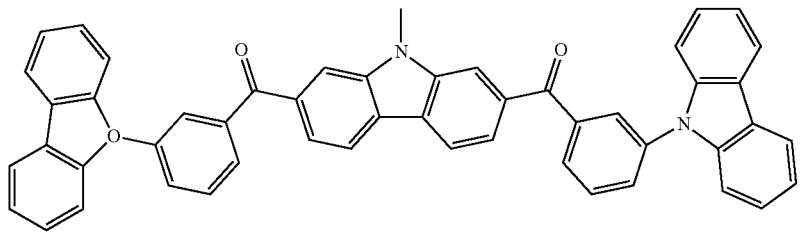
(27)
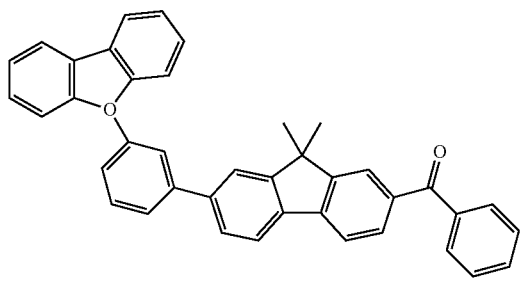
(28)
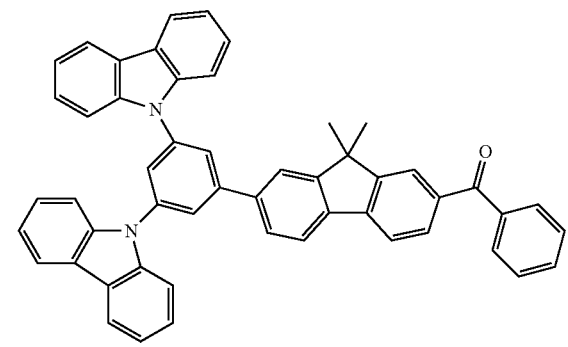
(29)
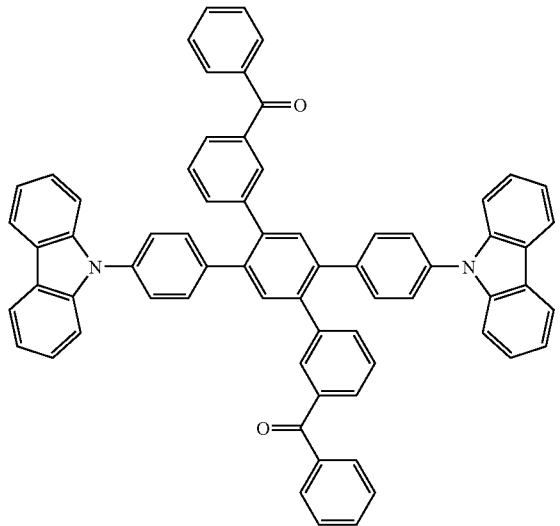
(30)
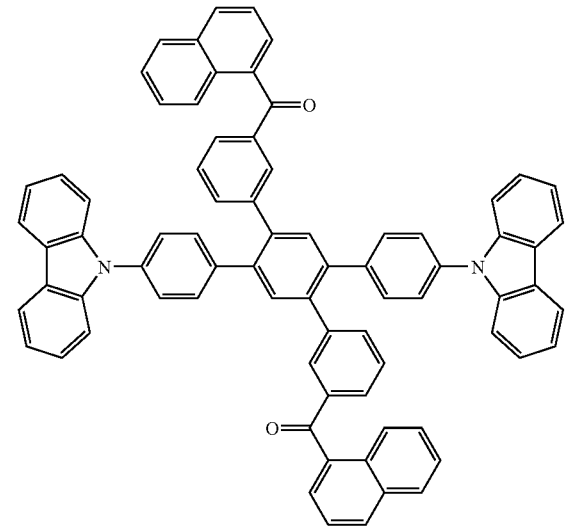

(31)
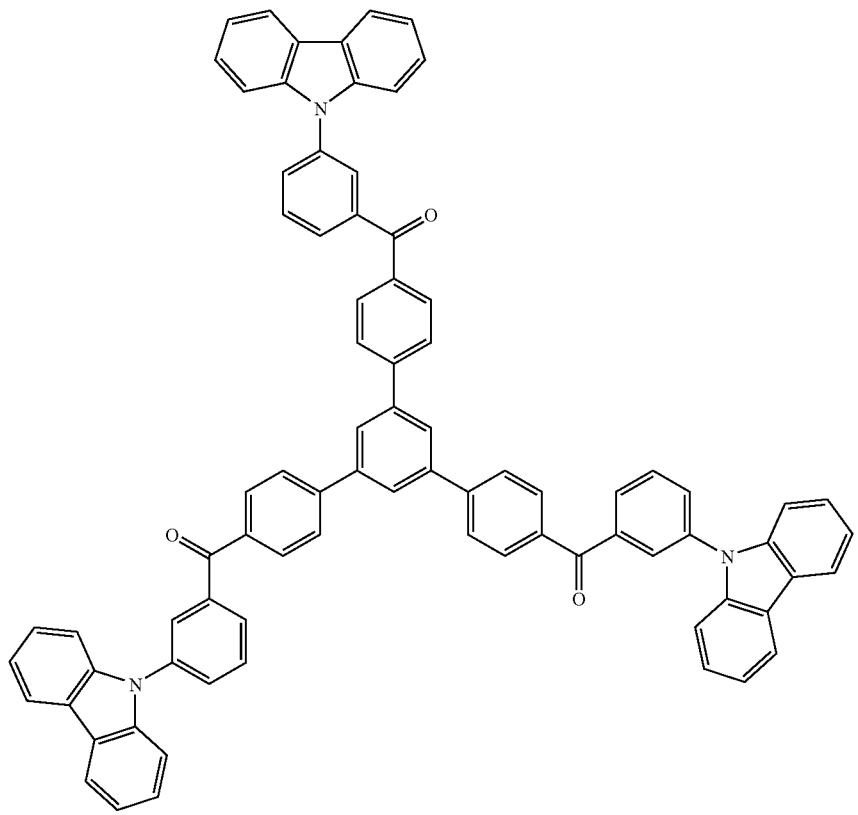
(32)
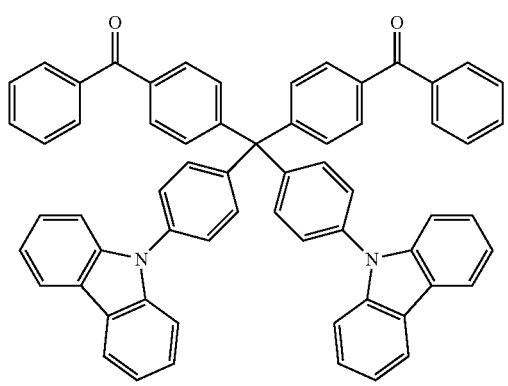
(33)
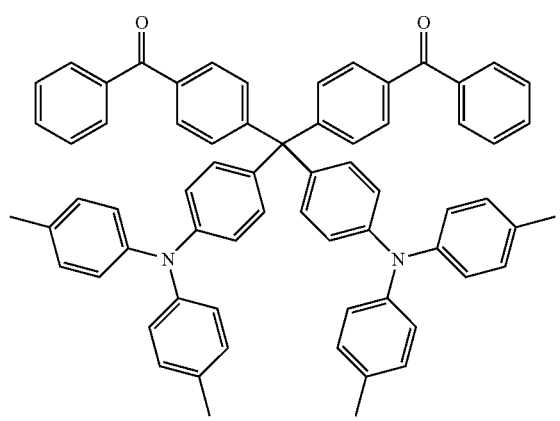
(34)
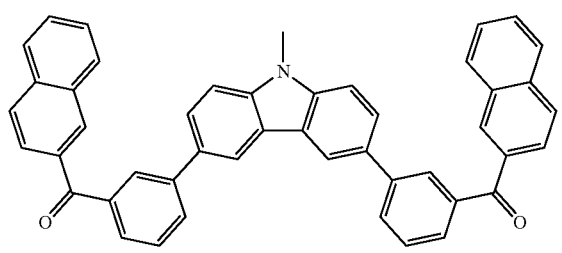
(35)
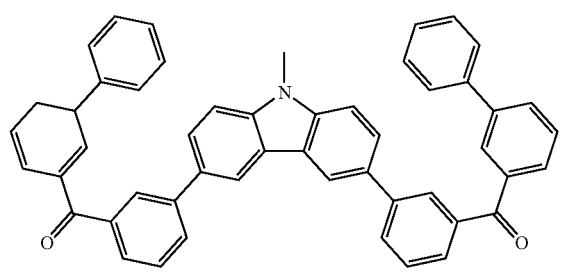

(36)
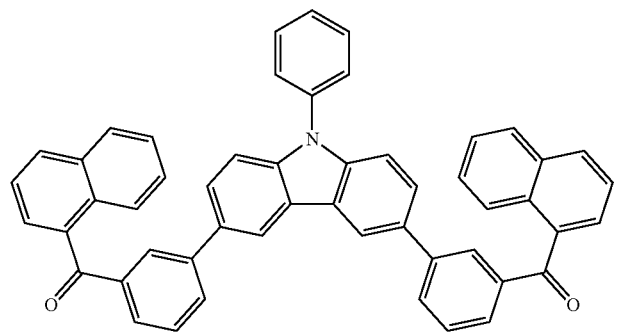
(37)
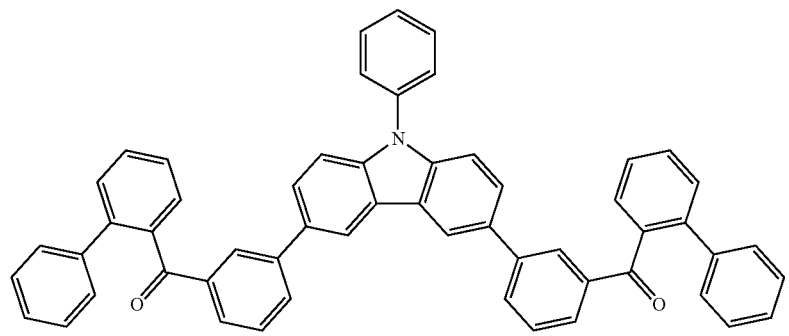
(38)
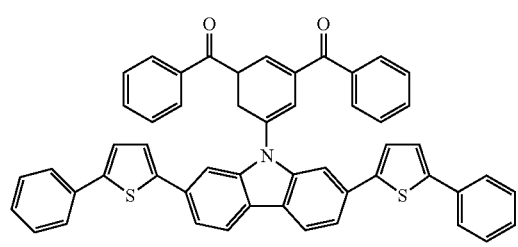
(39)
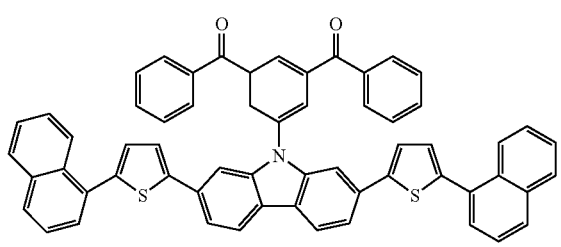
(40)
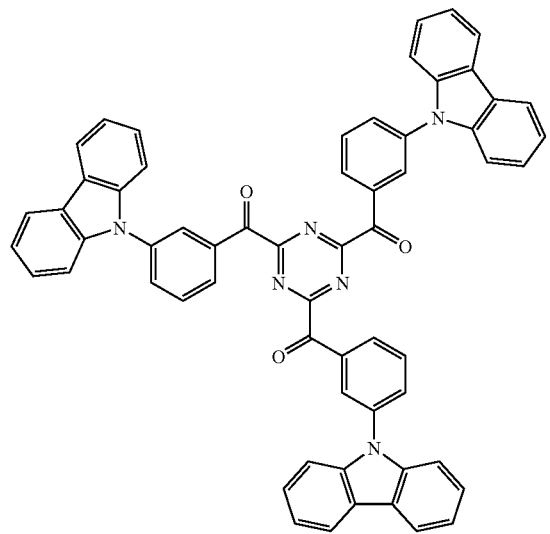
(41)
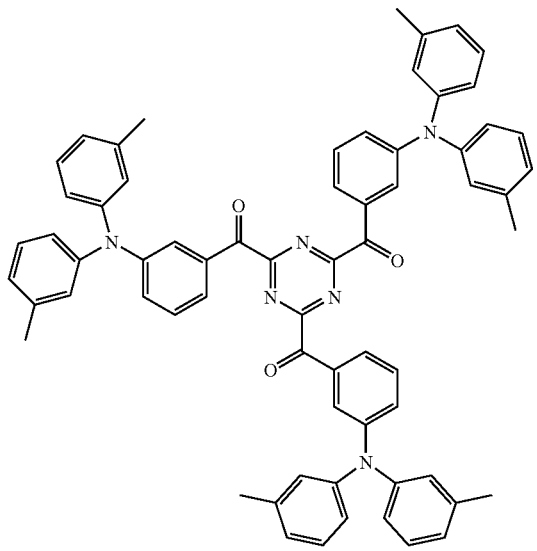

(42)
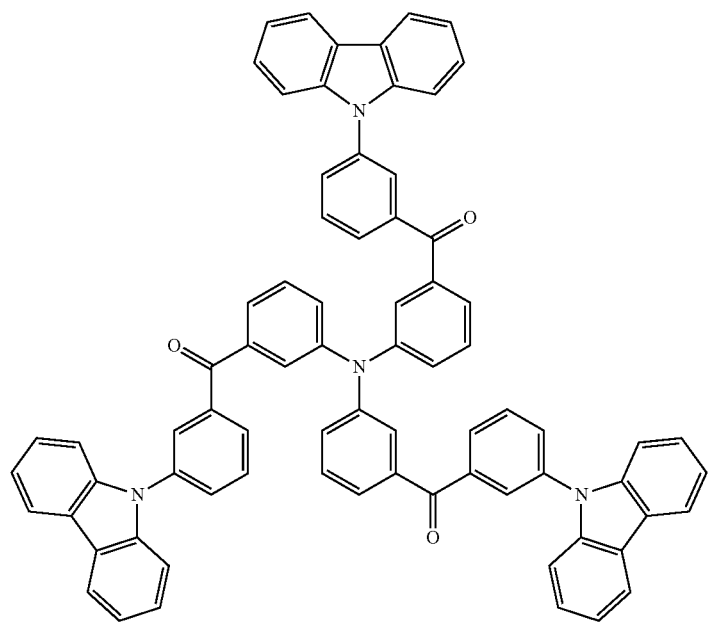
(43)
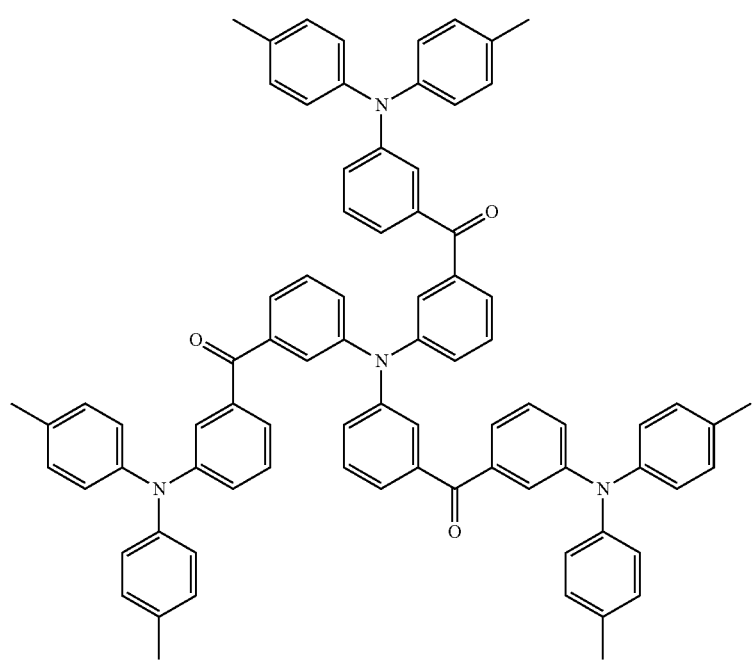

(44)
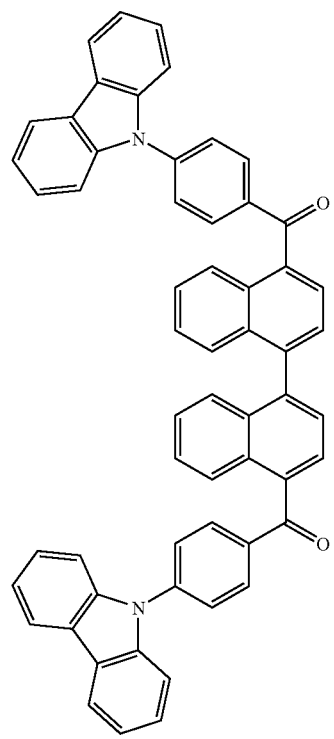
(45)
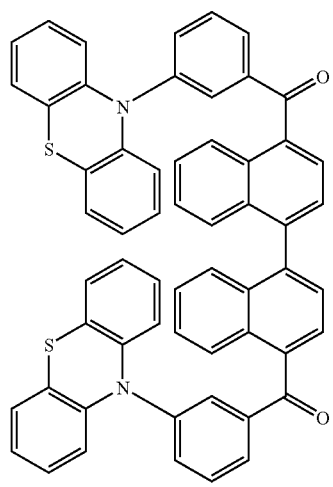
(46)
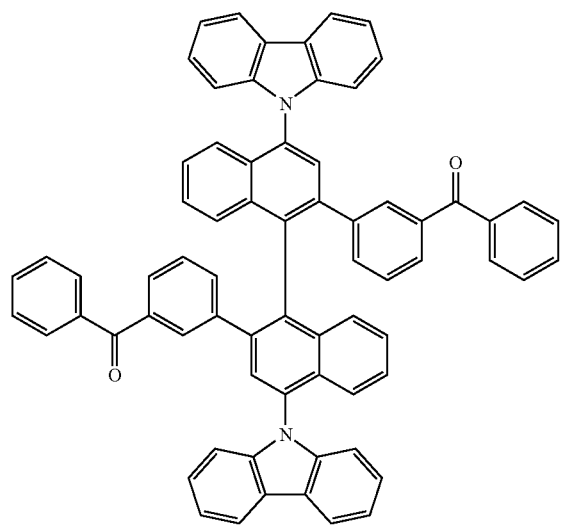
(47)
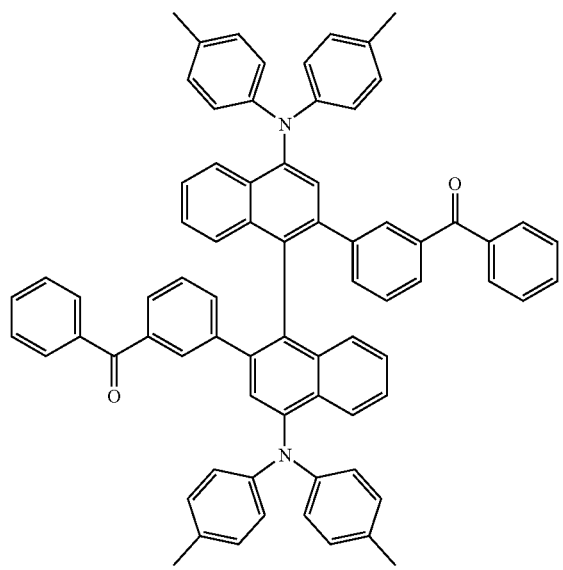

-continued
(48)
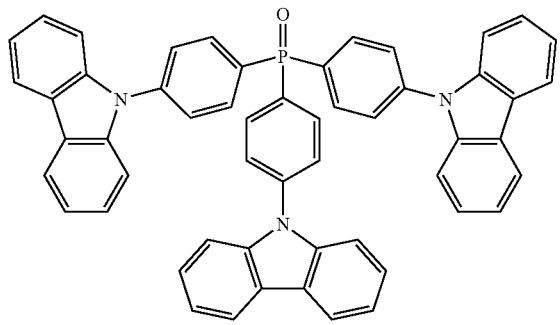
(49)
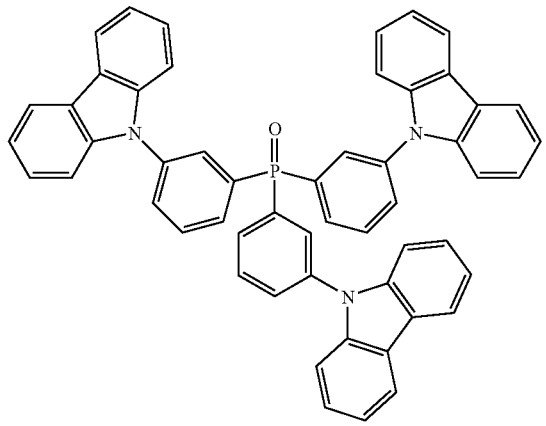
(50)
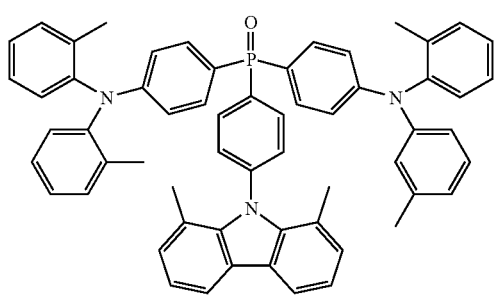
(51)
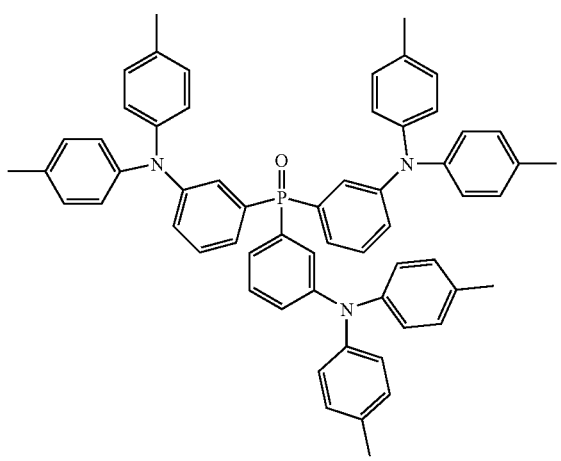
(52)
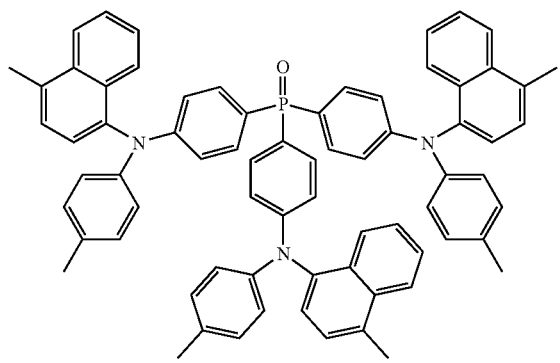
(53)
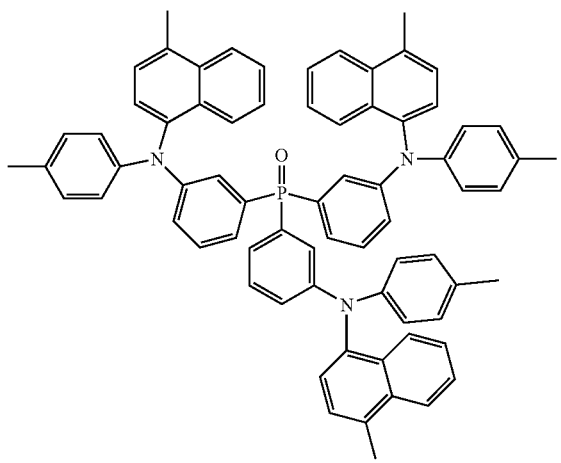

-continued
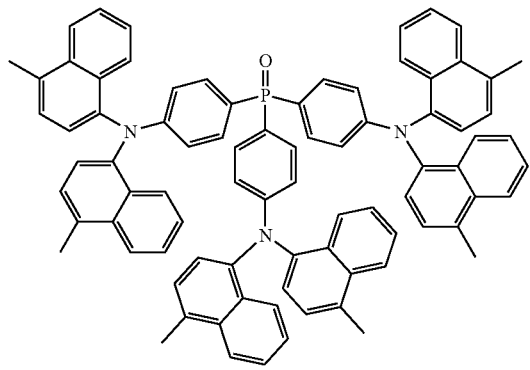
(54)
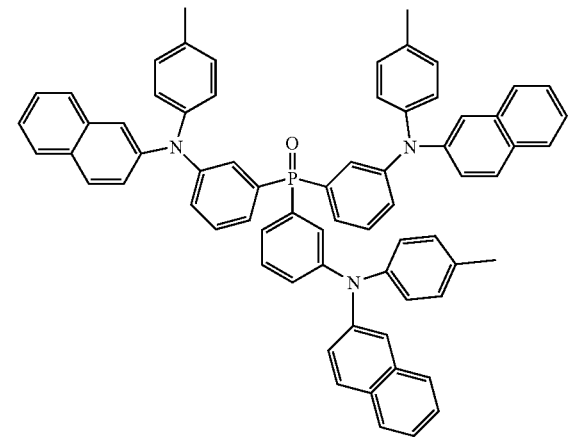
(55)
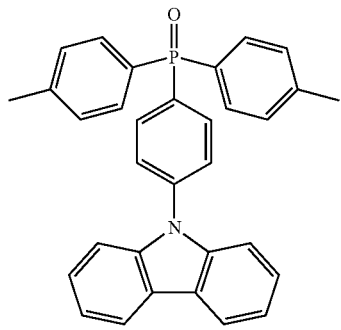
(56)
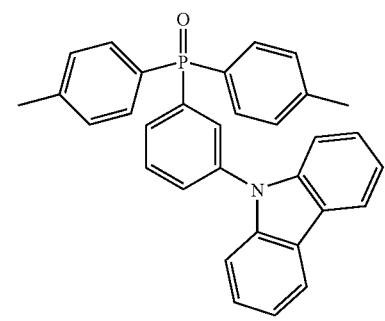
(57)
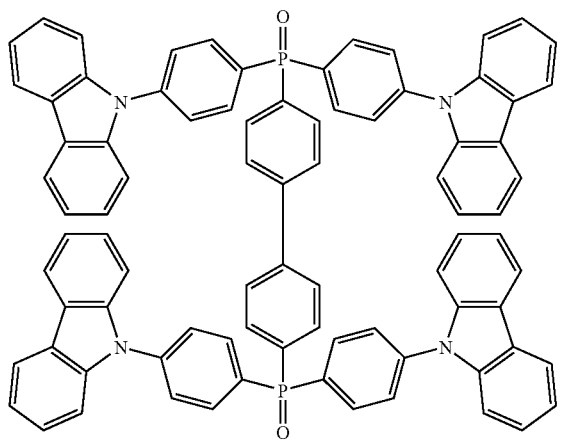
(58)
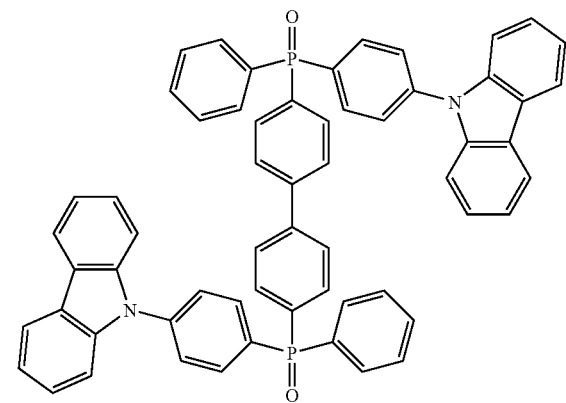
(59)
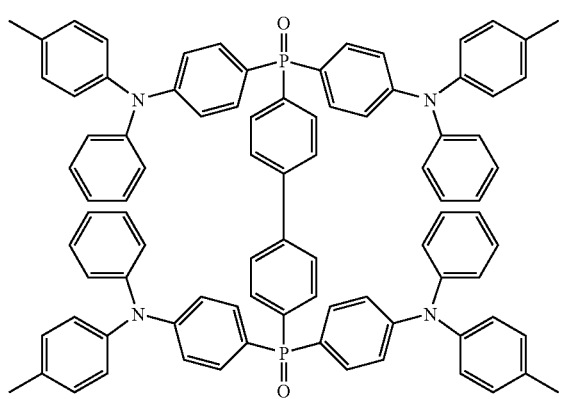
(60)
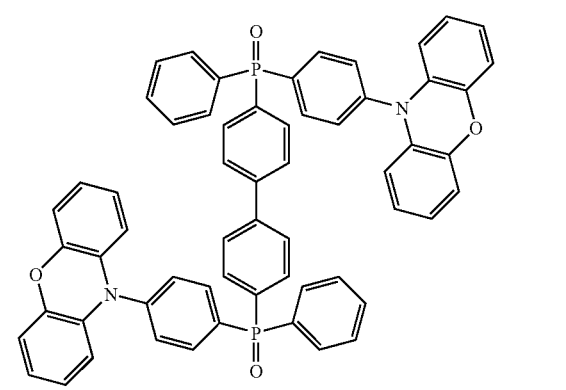
(61)

-continued
(62)
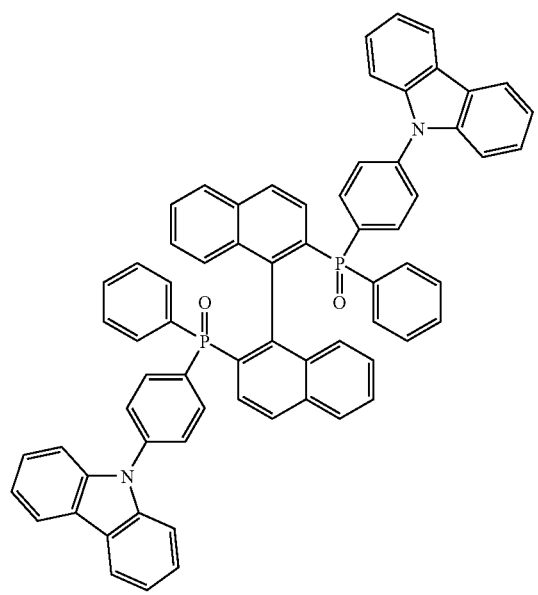
(63)
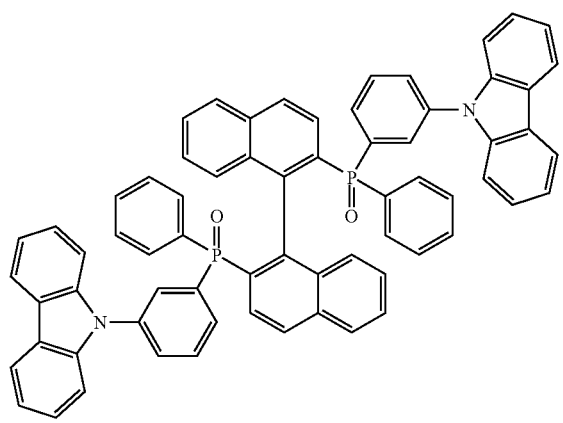
(64)
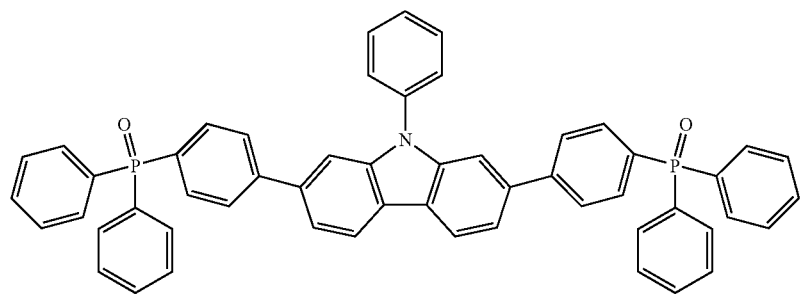
(65)
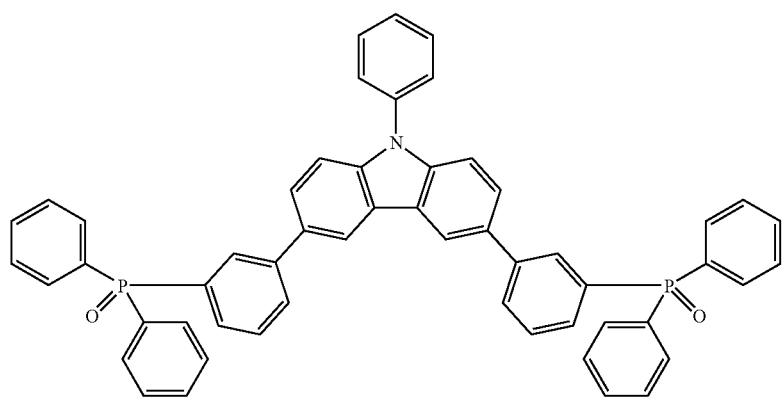

-continued
(66)
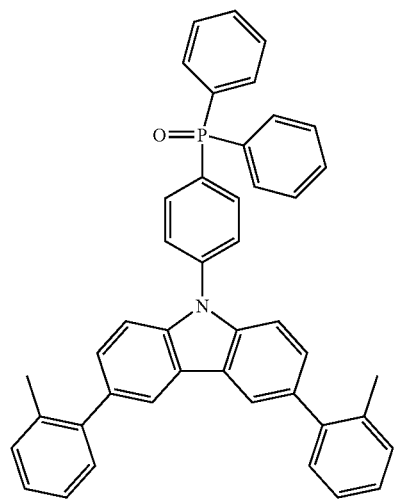
(67)
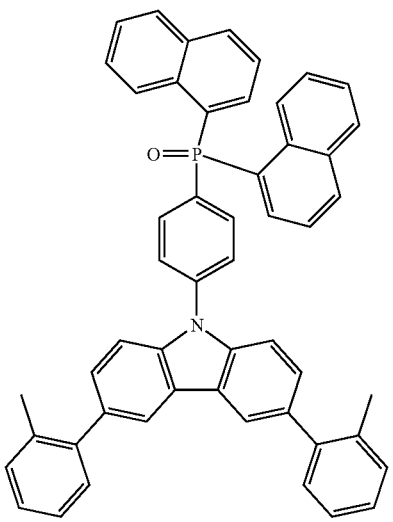
(68)
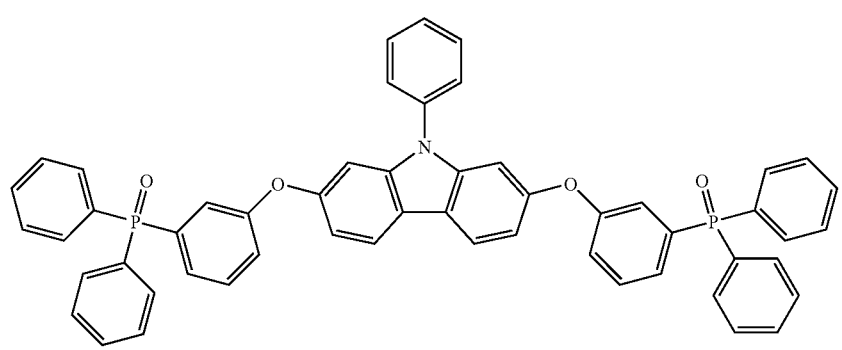
(69)
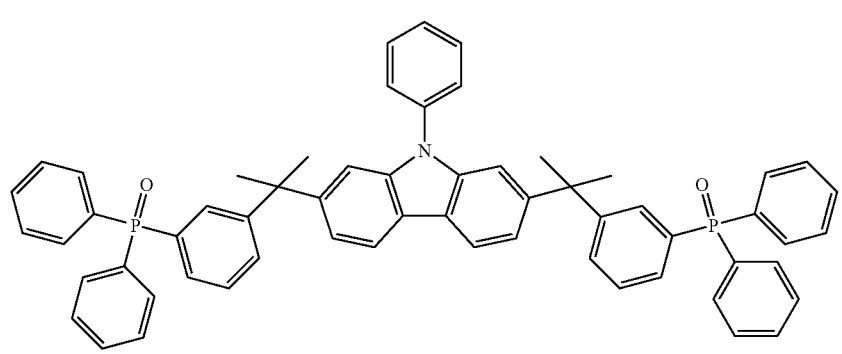
(70)
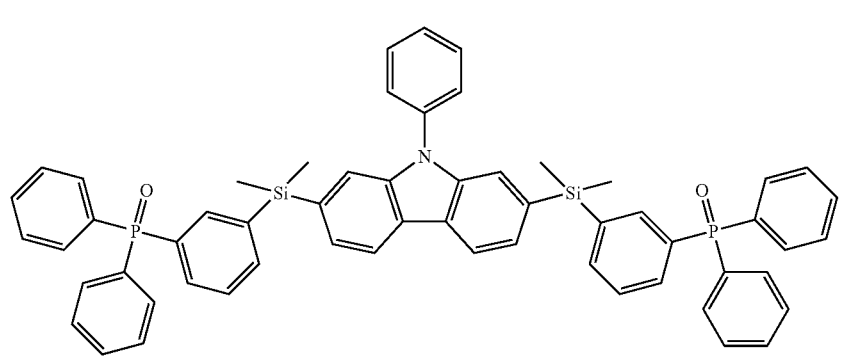

-continued
(71)
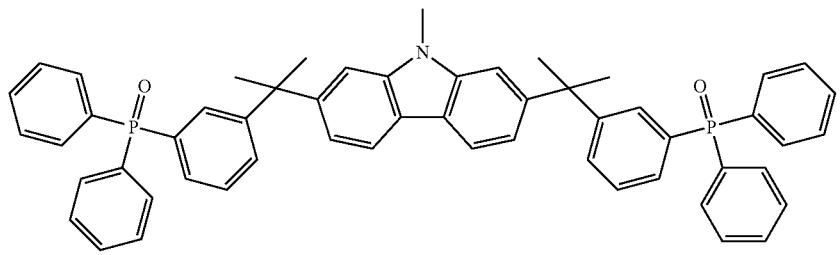
(72)
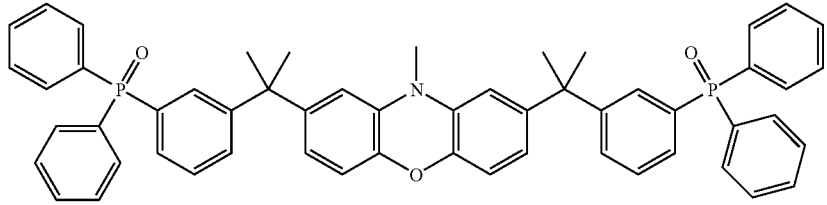
(73)
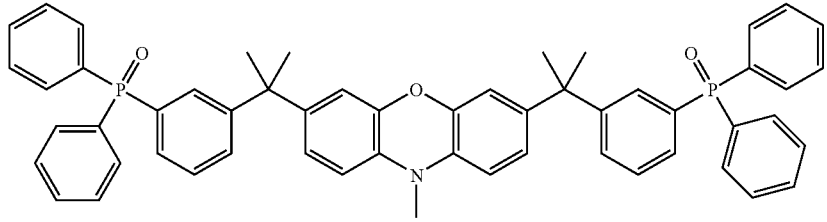
(74)
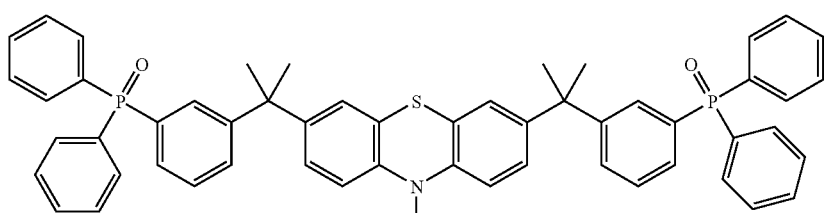
(75)
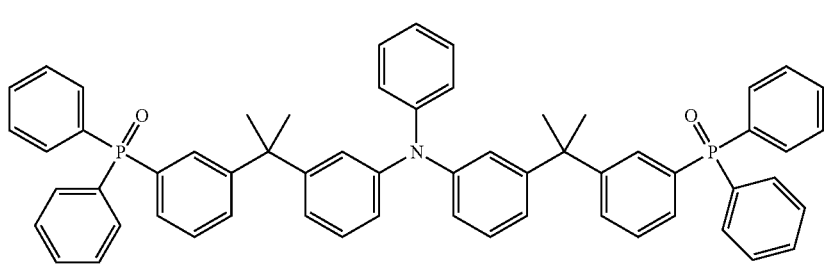
(76)
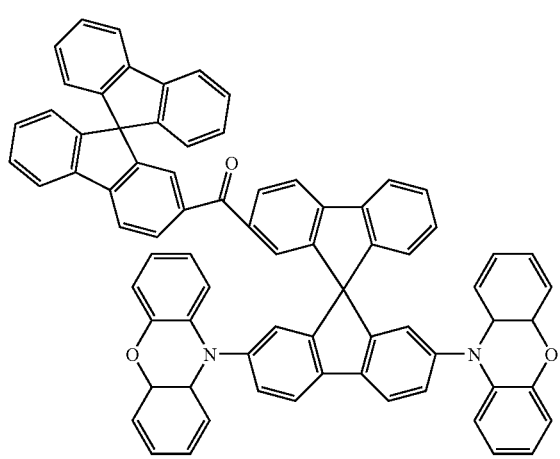
(77)
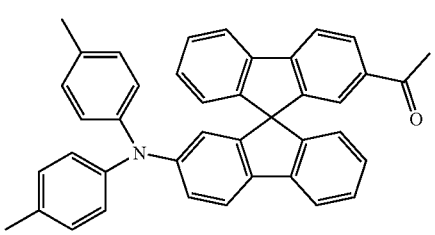

-continued
(78)
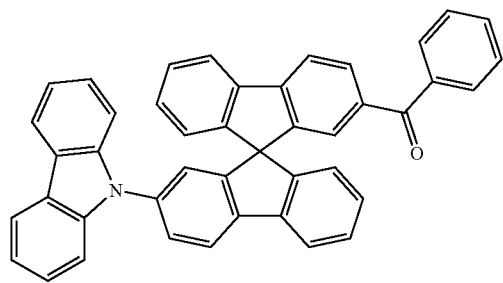
(79)
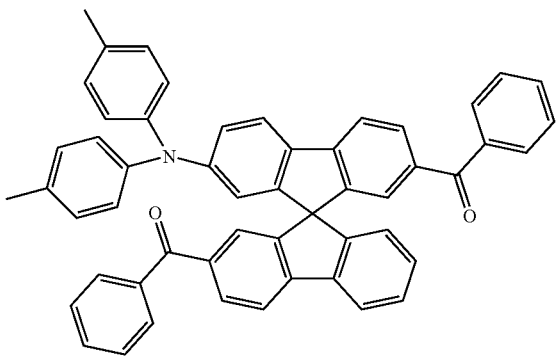
(80)
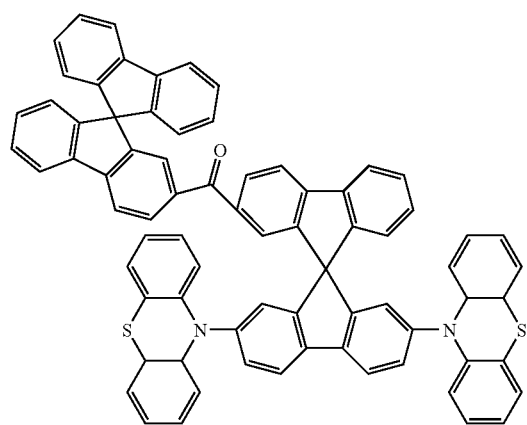
(81)
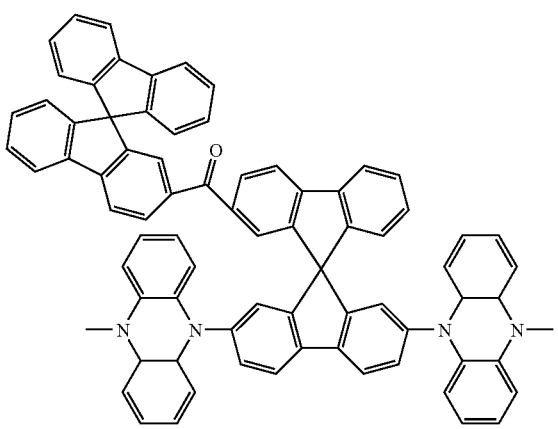
(82)
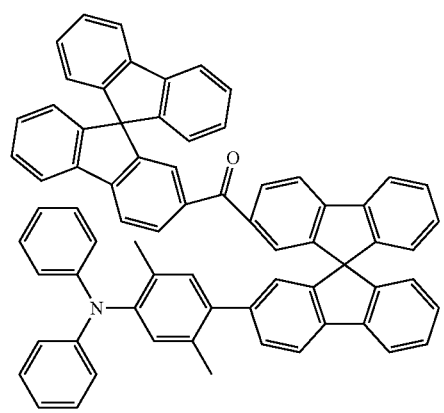
(83)
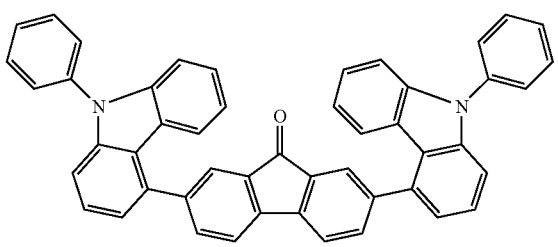

-continued
(84)
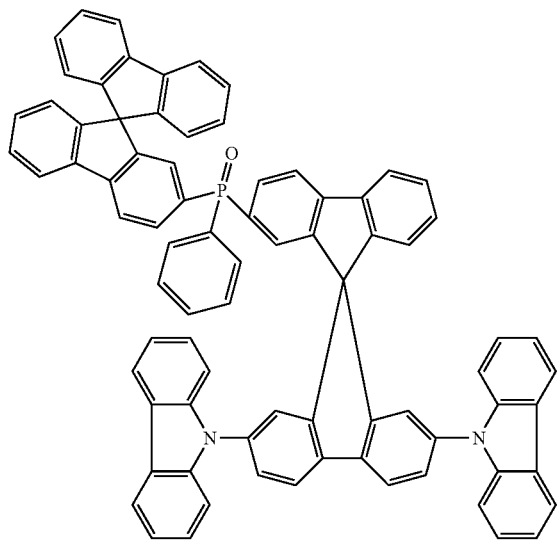
(85)
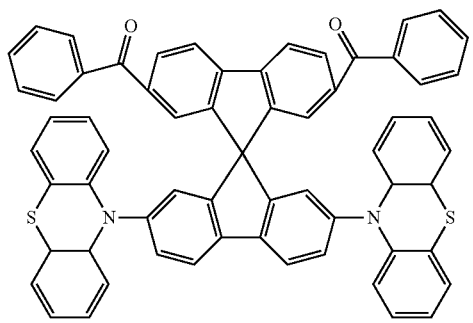
(86)
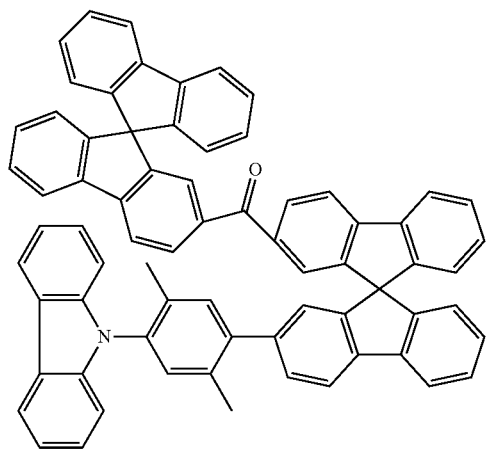
(87)
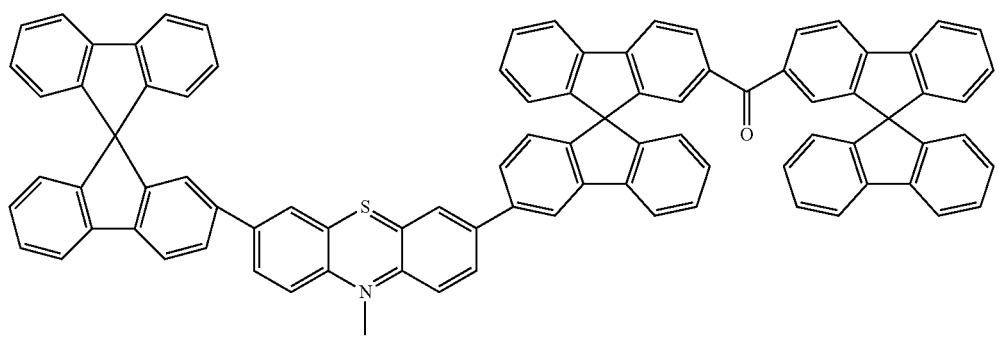

(88)
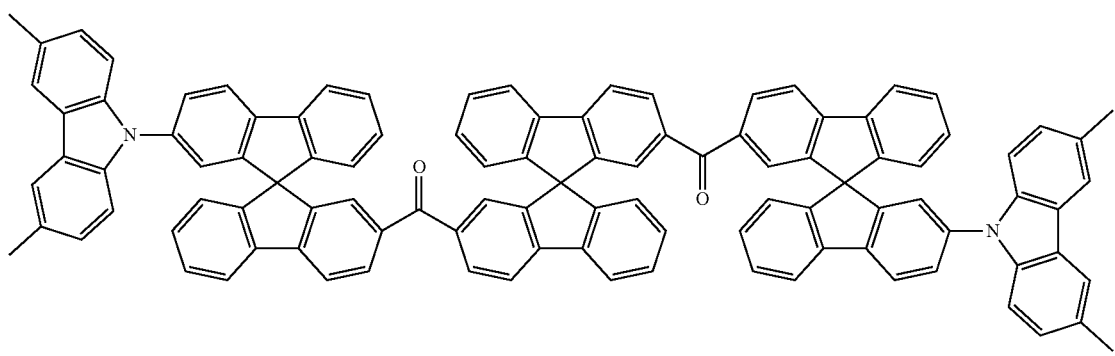
(89)
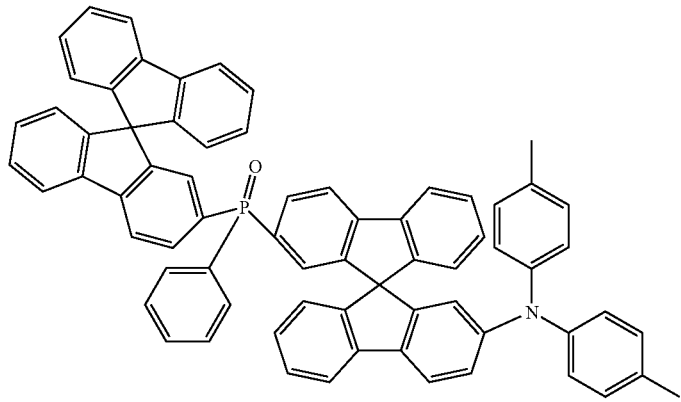
(90)
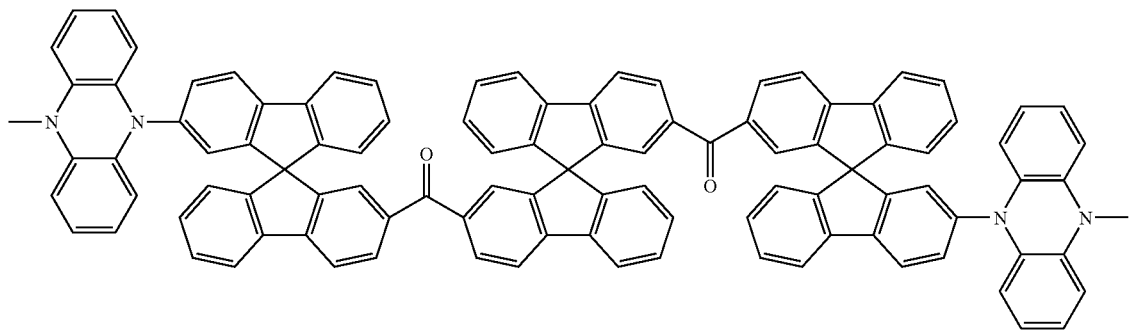
(91)
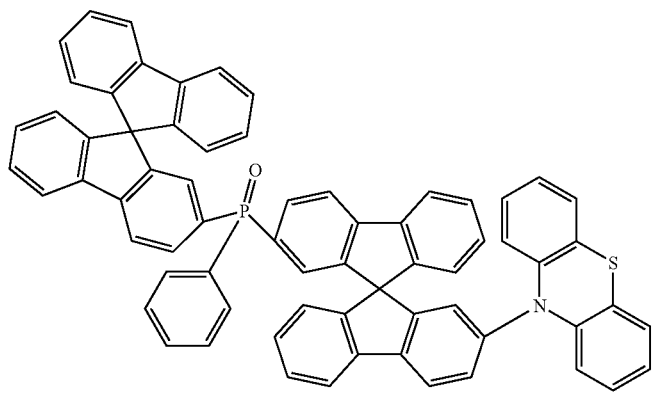

-continued
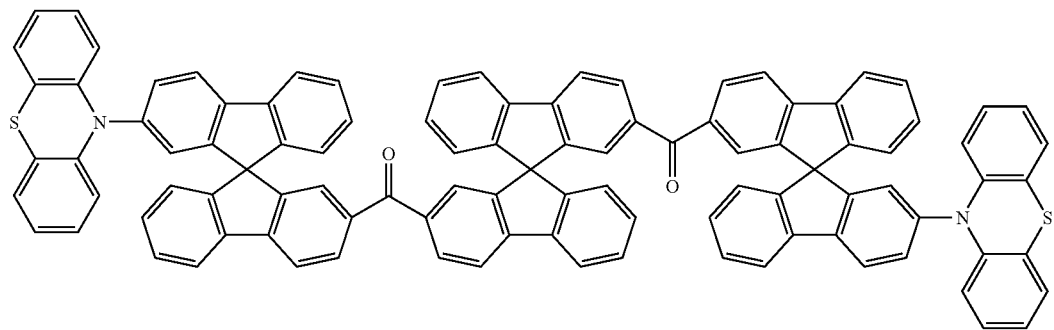
(92)
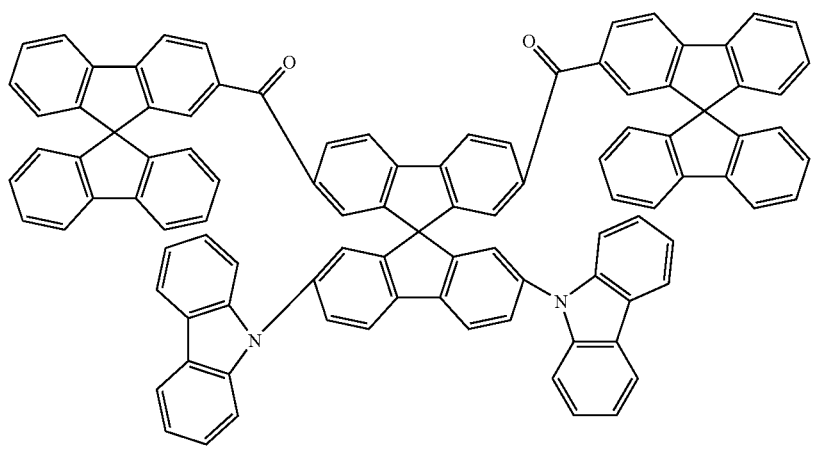
(93)
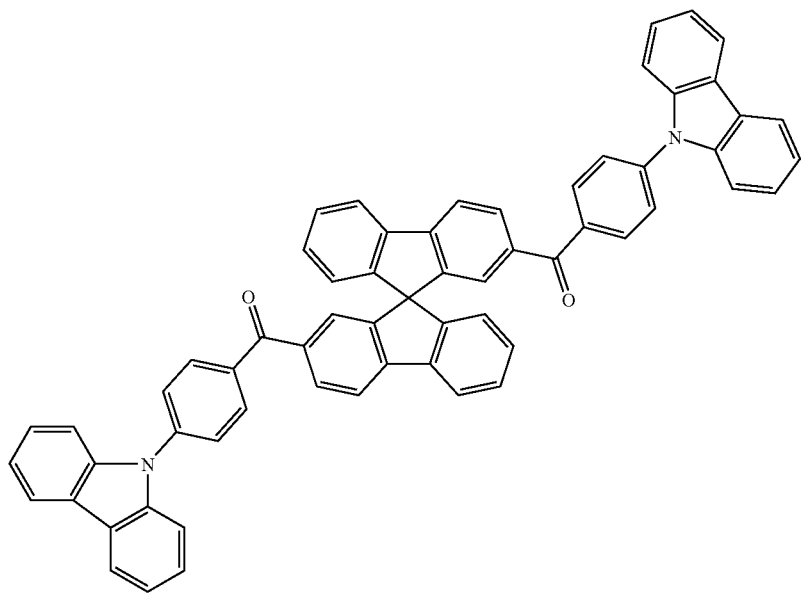
(94)

-continued
(95)
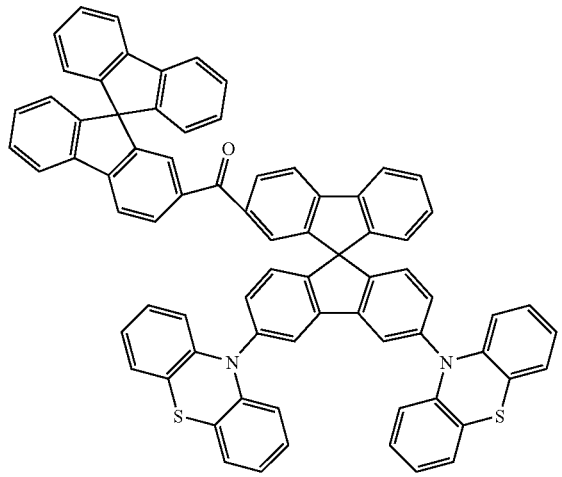
(96)
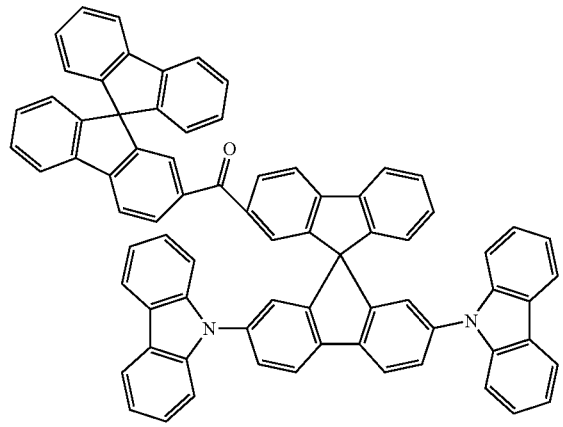
(97)
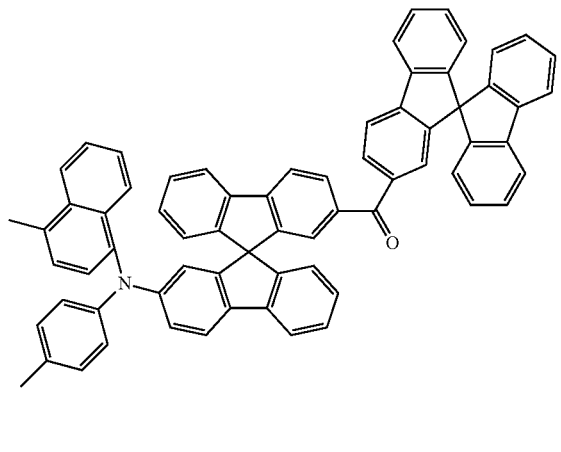
(98)
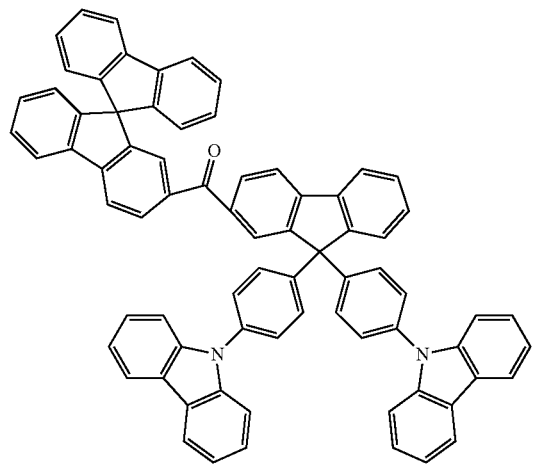
(99)
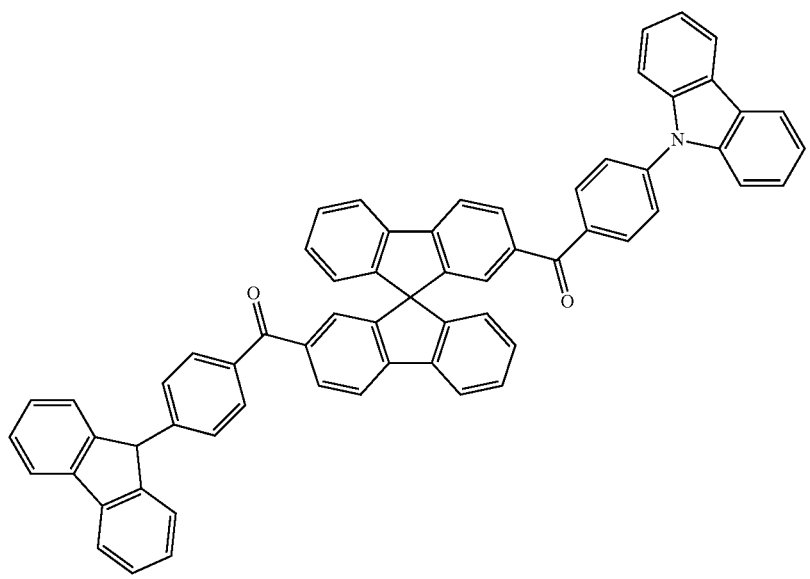

-continued
(100)
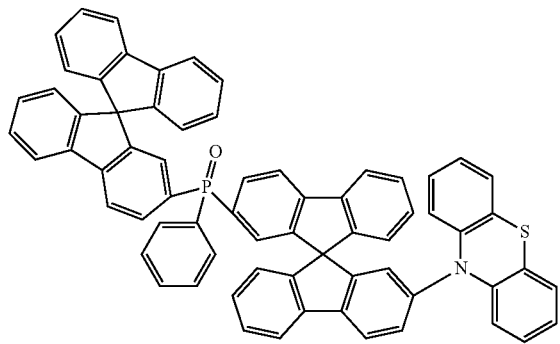
(101)
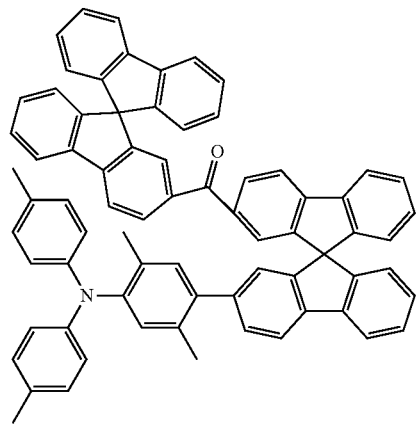
(102)
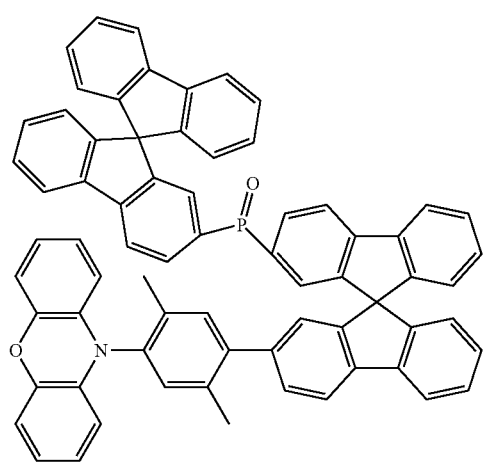
(103)
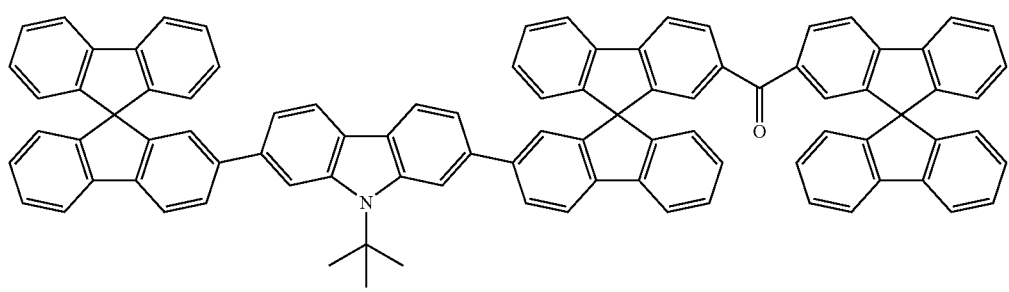

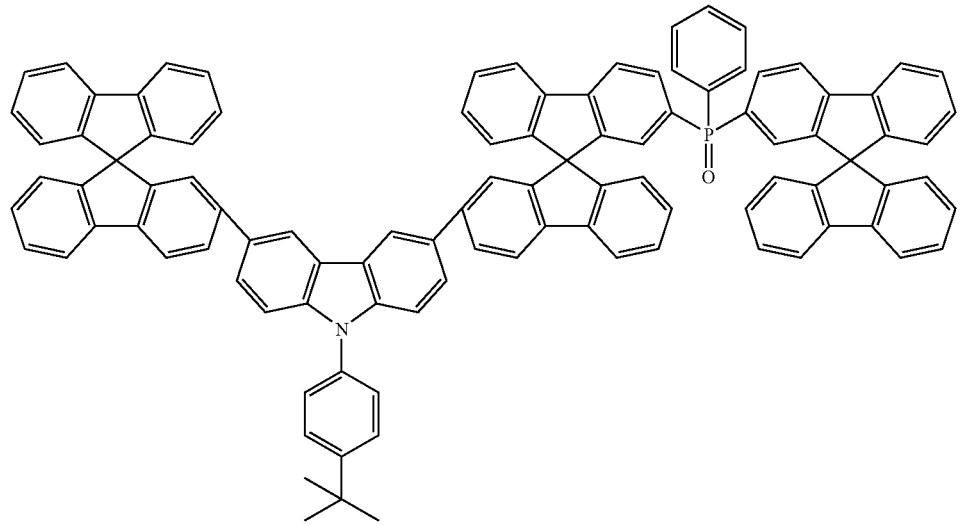
(104)
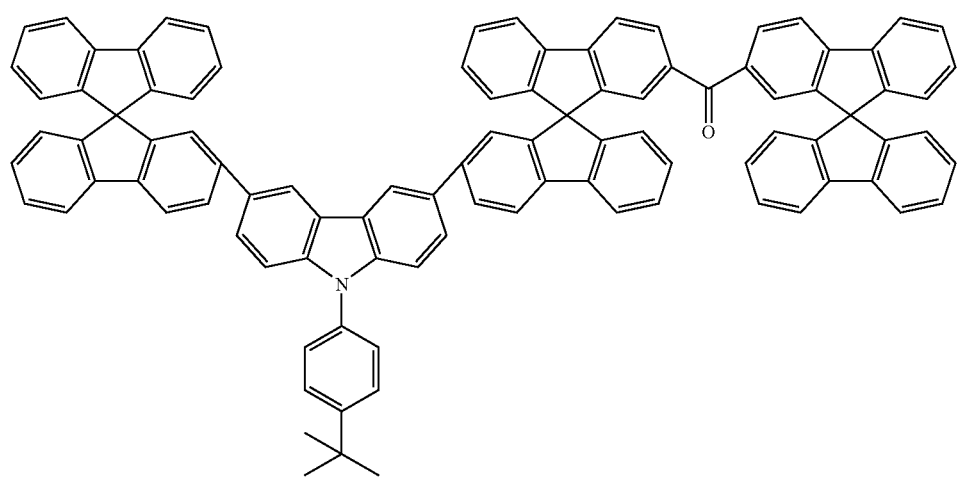
(105)
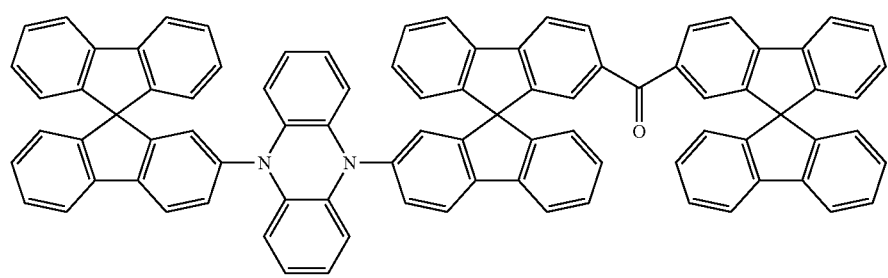
(106)
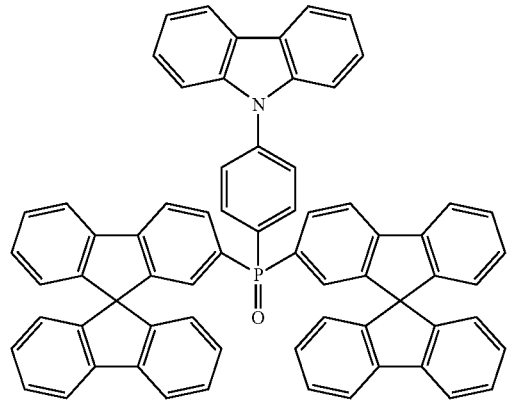
(107)

-continued
(108)
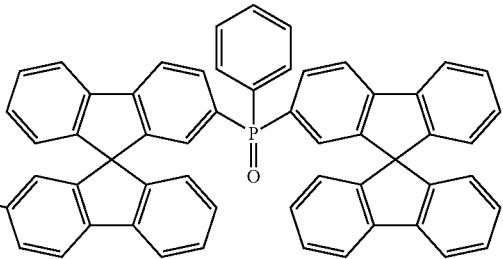
(109)
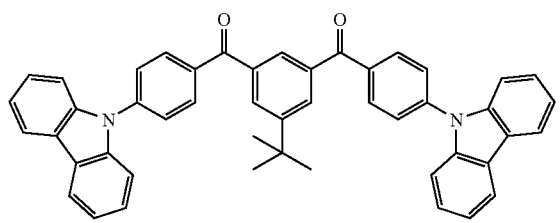
(110)
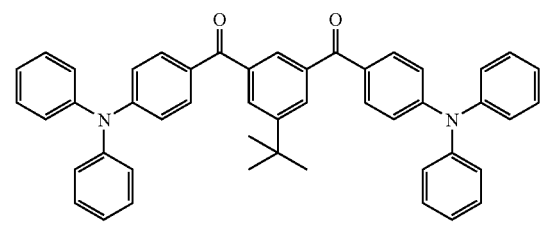
(111)
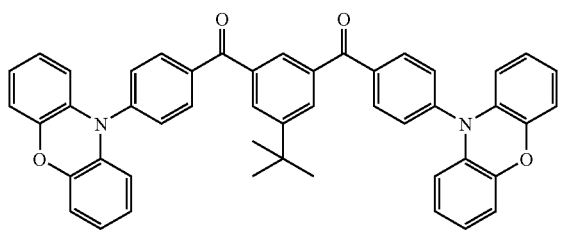
(112)
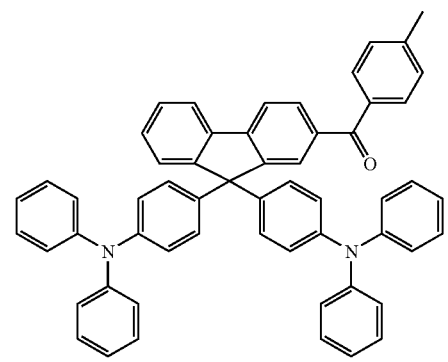
(113)
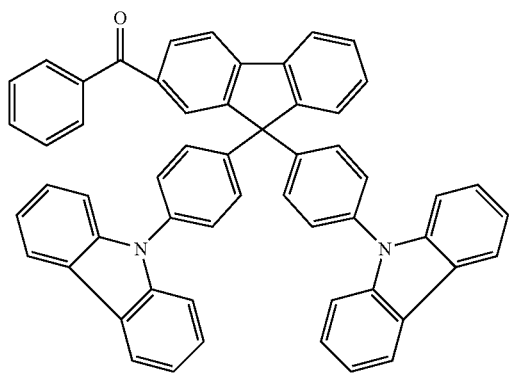
(114)
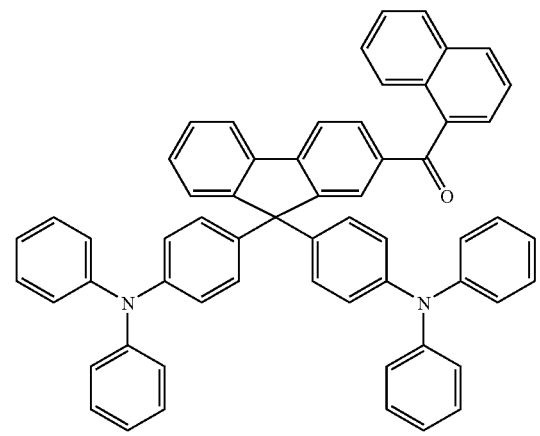

(115)
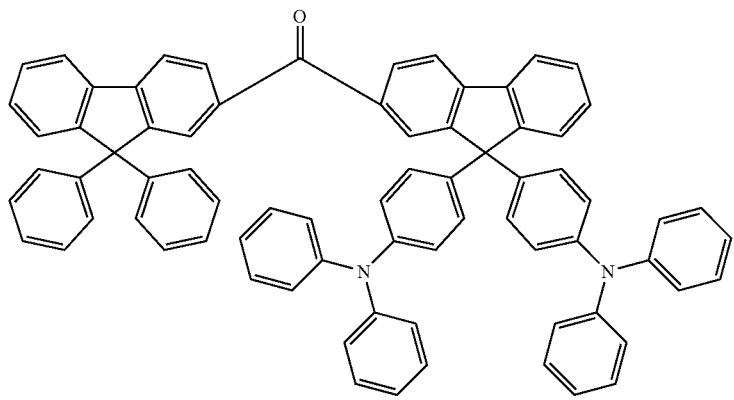
(116)
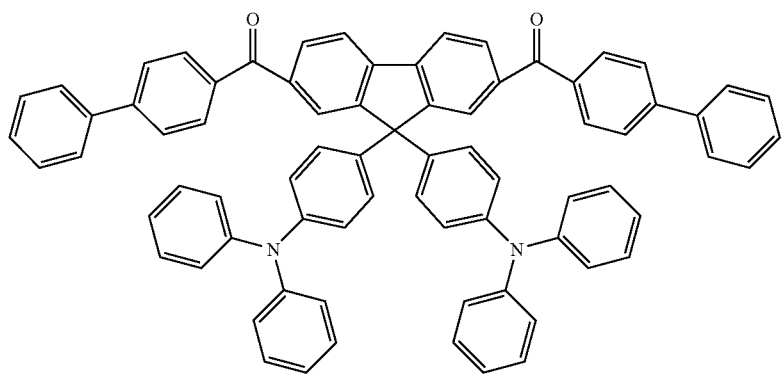
(117)
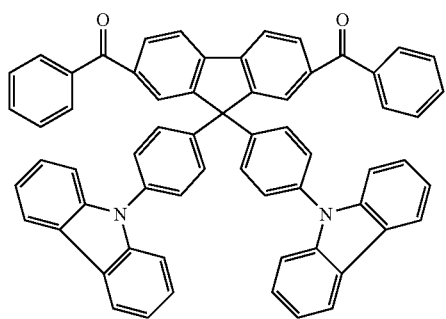
(118)
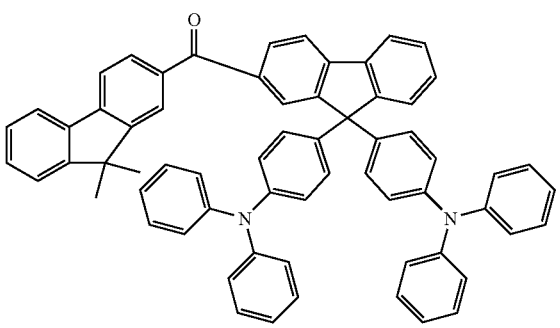
(119)
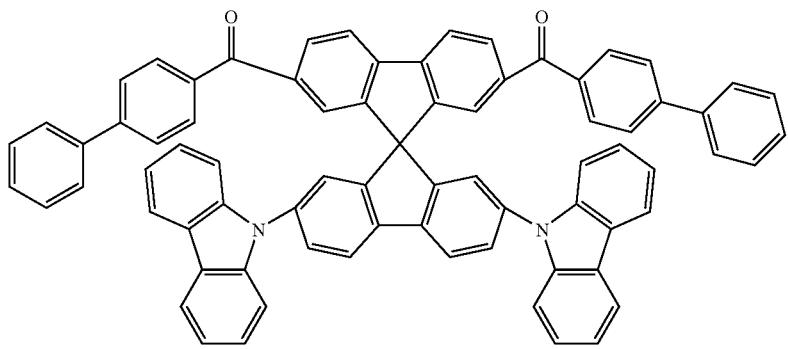

-continued
(120)
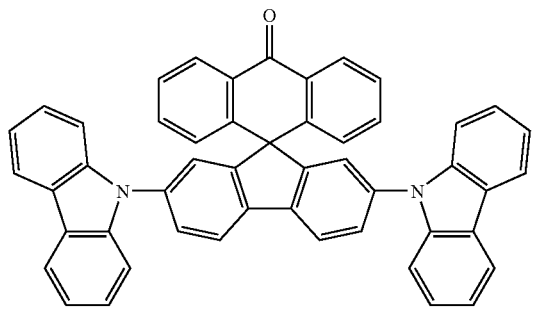
(121)
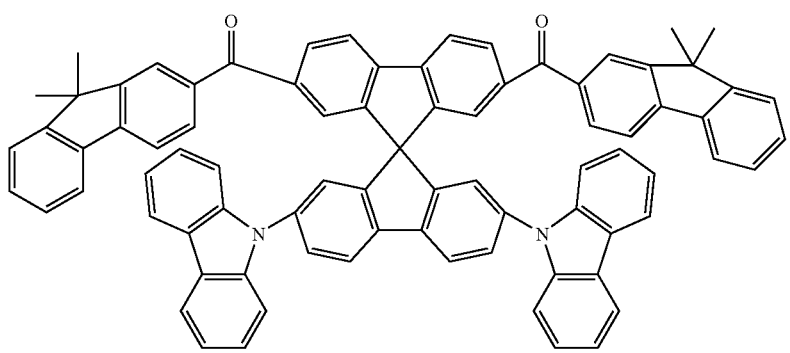
(123)
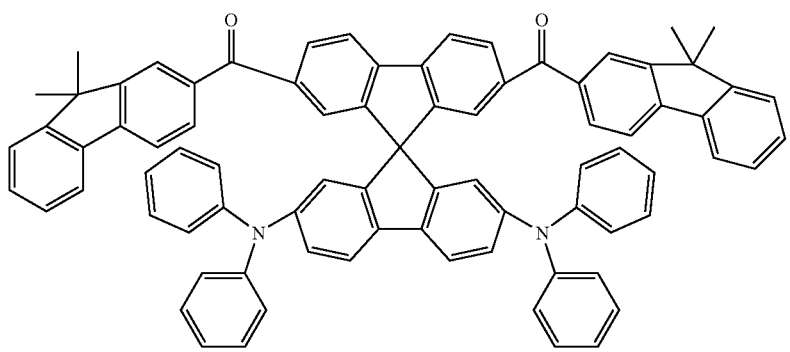
(124)
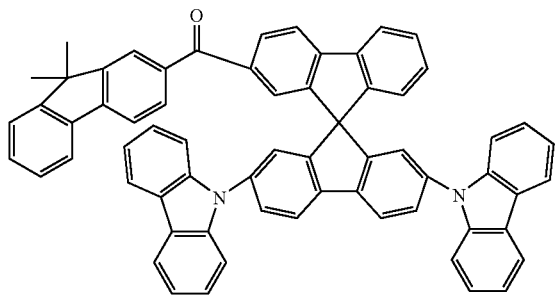
(125)
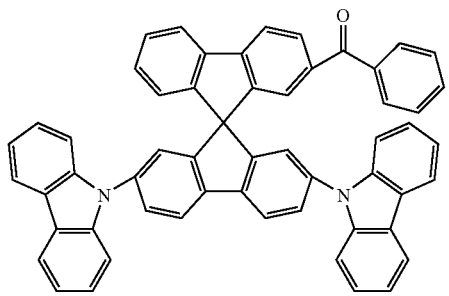

(126)
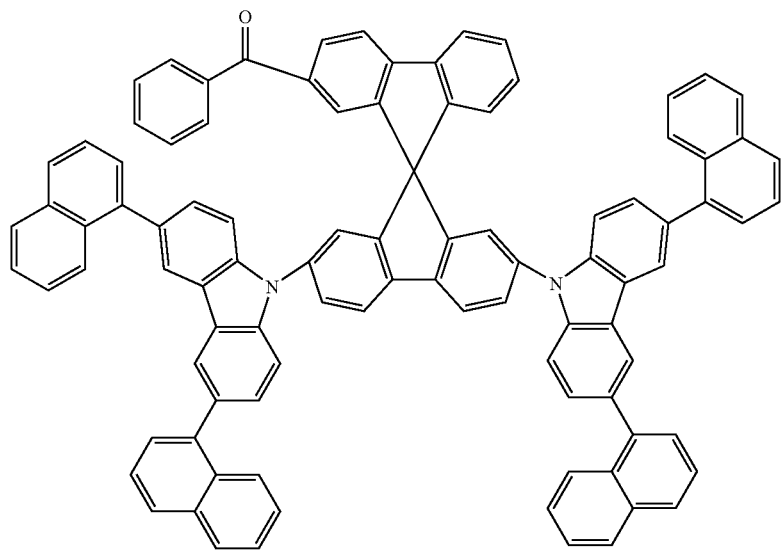
(127)
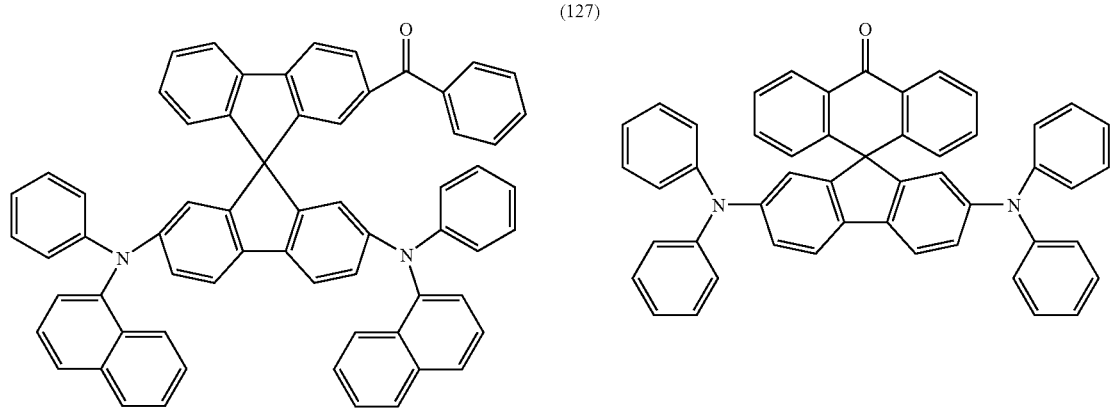
(128)
(129)
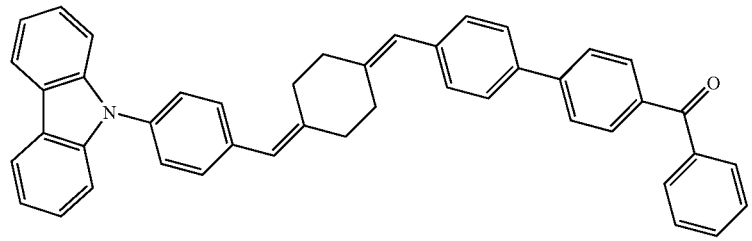
(130)
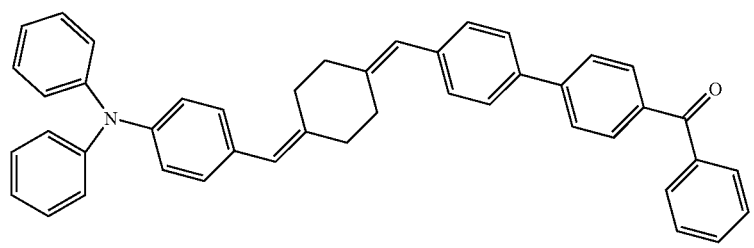
(131)
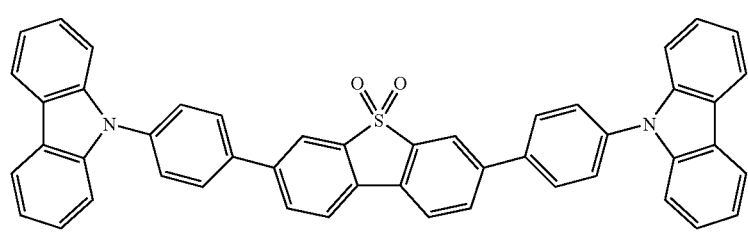

-continued
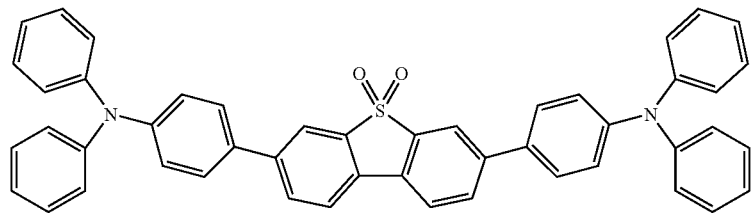
(132)
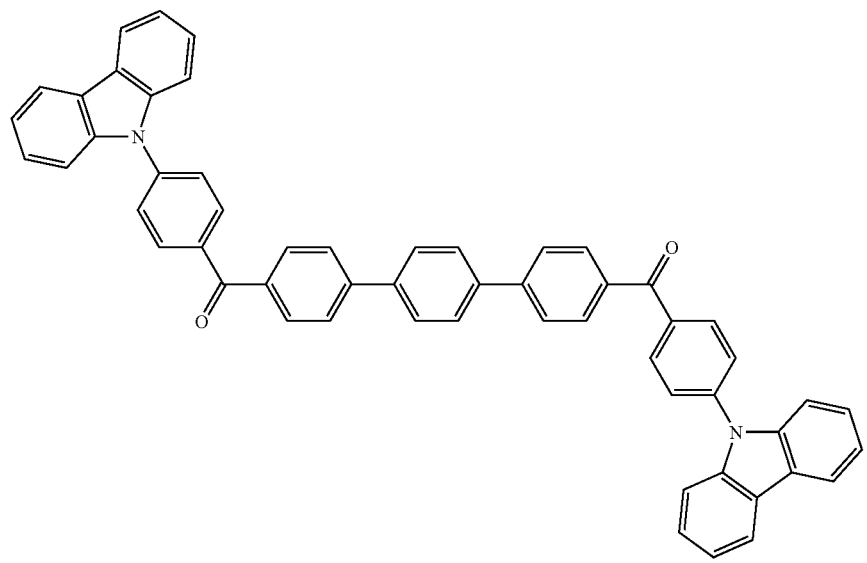
(133)
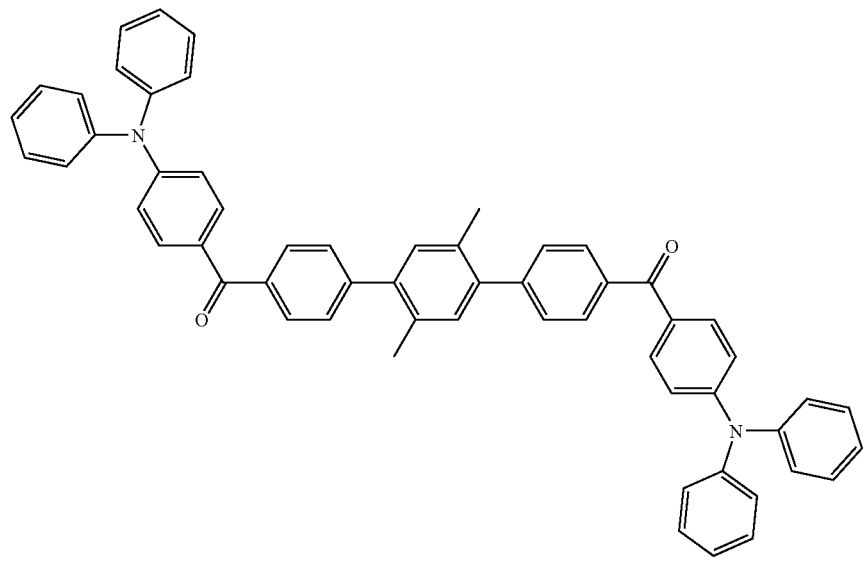
(134)

-continued
(135)
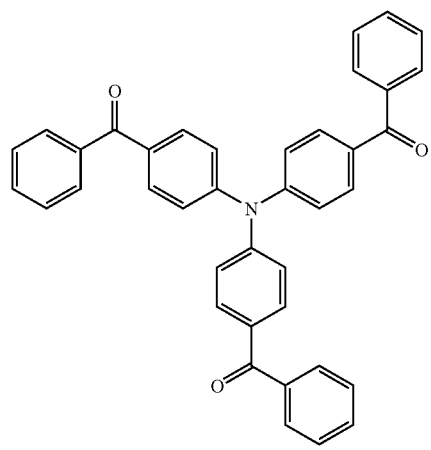
(136)
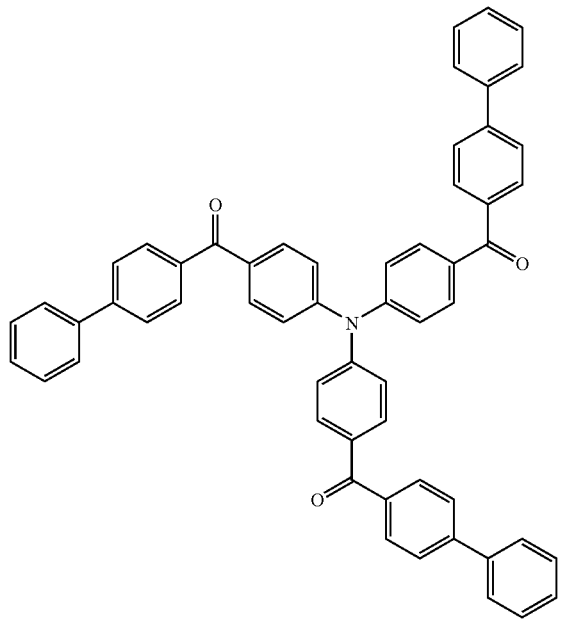
(137)
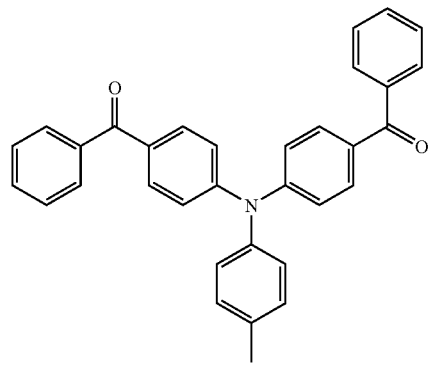
(138)
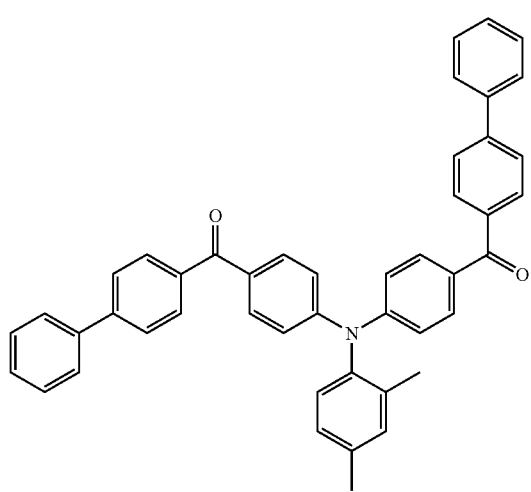

-continued (139)

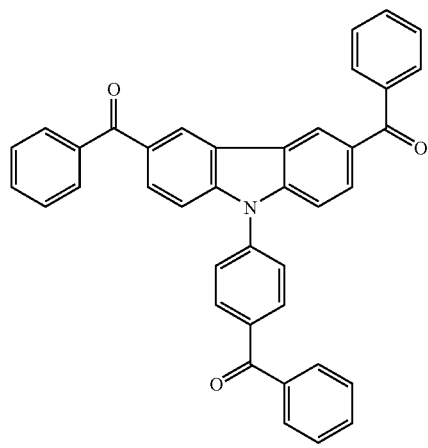

(140)

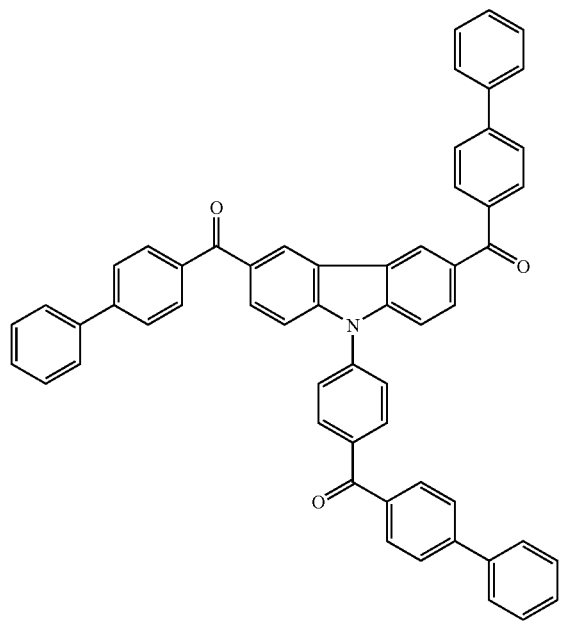

The compounds according to the invention, in particular compounds which are substituted by reactive leaving groups, such as bromine, iodine, triflate, tosylate, boronic acid or boronic acid ester, can also be used as monomers for the production of corresponding polymers, oligomers or as the core of dendrimers. The polymerisation here preferably takes place via the halogen or boronic acid functionality.

The invention thus furthermore relates to polymers, oligomers or dendrimers containing one or more structural elements of the formula (1), where one or more radicals $R^1$ represent bonds from the structural element of the formula (1) to the polymer, oligomer or dendrimer.

The same preferences as described above apply to the recurring units of the formula (1) or of the formulae (4) to (10).

These compounds are homopolymerised or copolymerised with further monomers. Suitable and preferred comonomers are selected from fluorenes (for example as described in EP 842208 or WO 00/22026), spirobifluorenes (for example as described in EP 707020, EP 894107 or WO 06/061181), para-phenylenes (for example as described in WO 92/18552), carbazoles (for example as described in WO 04/070772 or WO 04/113468), thiophenes (for example as described in EP 1028136), dihydrophenanthrenes (for example as described in WO 05/014689), cis- and trans-indenofluorenes (for example as described in WO 04/041901 or WO 04/113412), ketones (for example as described in WO 05/040302), phenanthrenes (for example as described in WO 05/104264 or the unpublished application DE 102005037734.3) or also a plurality of these units. These polymers may also contain further units, for example emitting units, such as, for example, phosphorescent metal complexes (for example as described in WO 06/003000), and/or charge-transport units, in particular those based on triarylamines. The emitting units, for example the phosphorescent metal complexes, may also be admixed with the polymer.

The compounds according to the invention can be synthesised by standard methods of organic chemistry. Thus, it is possible to build up aromatic ketones, for example, by Friedel-Crafts acylation. Aromatic ketones can furthermore be synthesised by reaction of an aromatic nitrile with an aromatic organometallic compound, for example an aryl-lithium compound or an aromatic Grignard reagent, followed by hydrolysis of the imine formed as an intermediate. These ketones can be functionalised, for example brominated, and reacted in a further step with an aromatic amine, for example with carbazole or a diarylamine, in a Hartwig-Buchwald coupling to give the compounds according to the invention.

The present invention therefore furthermore relates to a process for the synthesis of the compounds according to the invention by Hartwig-Buchwald coupling of an aromatic ketone which is substituted by one or more halogens, preferably bromine or iodine, or a group $OSO_2R^2$, preferably triflate or tosylate, to a diarylamino compound, where the two aryl groups may also be bridged by a group E.

The brominated compounds can furthermore be employed, either directly or after conversion into a boronic acid derivative, as monomers for the production of polymers, oligomers or dendrimers.

The compounds according to the invention and the corresponding polymers, oligomers and dendrimers are suitable for use in organic electroluminescent devices (OLEDs, PLEDs), in particular as triplet matrix materials.

The invention therefore furthermore relates to the use of compounds containing at least one structural element of the formula (1) or compounds of the formulae (4) to (10) and corresponding polymers, oligomers and dendrimers in organic electronic devices, in particular in organic electroluminescent devices.

The invention still further relates to organic electronic devices comprising at least one compound containing at least one structural element of the formula (1) or compounds of the formulae (4) to (10) or at least one corresponding polymer, oligomer or dendrimer, in particular organic electroluminescent devices comprising anode, cathode and at least one emitting layer, characterised in that at least one layer comprises at least one compound which contains at least one structural element of the formula (1) or at least one compound of the formulae (4) to (10).

Apart from the cathode, anode and the emitting layer, the organic electroluminescent device may also comprise further layers, for example in each case one or more hole-injection layers, hole-transport layers, electron-transport layers, electron-injection layers and/or charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*). It is likewise possible for interlayers, which have, for example, an exciton-blocking function, to be introduced between two emitting layers. However, it should be pointed out that each of these layers does not necessarily have to be present.

In a further preferred embodiment of the invention, the organic electroluminescent device comprises a plurality of emitting layers, where at least one layer comprises at least one compound according to the invention or at least one corresponding polymer, oligomer or dendrimer. These emission layers particularly preferably have in total a plurality of emission maxima between 380 nm and 750 nm, resulting overall in white emission, i.e. various emitting compounds which are able to fluoresce or phosphoresce and emit yellow, orange or red light are used in the emitting layers. Particular preference is given to three-layer systems, where at least one of these layers comprises at least one compound according to the invention or at least one corresponding polymer, oligomer or dendrimer and where the three layers exhibit blue, green and orange or red emission (for the basic structure, see, for example, WO 05/011013). Likewise suitable for white emission are emitters which have broad-band emission bands and thus exhibit white emission.

In order to be used as functional material, the compounds according to the invention or mixtures thereof or polymers or dendrimers containing structural elements of the formula (1) or mixtures thereof, optionally together with emitting compounds and/or also further compounds, are applied to a substrate by generally known methods which are familiar to the person skilled in the art, such as vacuum evaporation, evaporation in a carrier-gas stream or from solution by spin coating or using various printing processes (for example ink-Jet printing, offset printing, LITI printing, etc.), in the form of a film. The use of printing processes and other solution-based processes can have advantages with respect to the scalability of production, and also with respect to the setting of mixing ratios in the blend layers used. Due to the good solubility and good film-formation properties, the compounds according to the invention are also particularly suitable for the production of organic electronic devices from solution.

In a preferred embodiment of the invention, the compounds according to the invention or the corresponding polymers, oligomers or dendrimers are employed as matrix for phosphorescent dopants. These phosphorescent emitters comprise at least one compound which emits light, preferably in the visible region, on suitable excitation and in addition contains at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium.

Particularly preferred organic electroluminescent devices comprise, as phosphorescent emitters, at least one compound of the formulae (18) to (21)

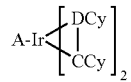
Formula (18)

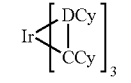
Formula (19)

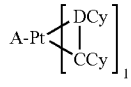
Formula (20)

Formula (21)

where $R^1$ has the same meaning as described above, and the following applies to the other symbols used:

DCy is, identically or differently on each occurrence, a cyclic group which contains at least one donor atom, preferably nitrogen or phosphorus, via which the cyclic group is bonded to the metal, and which may in turn carry one or more substituents $R^1$; the groups DCy and CCy are connected to one another via a covalent bond;

CCy is, identically or differently on each occurrence, a cyclic group which contains a carbon atom via which the cyclic group is bonded to the metal and which may in turn carry one or more substituents $R^1$;

A is, identically or differently on each occurrence, a monoanionic, bidentate chelating ligand, preferably a diketonate ligand.

It is also possible here for a bridge to be present between the groups DCy and CCy through the formation of ring systems between a plurality of radicals $R^1$.

Examples of the emitters described above can be found in the applications WO 00/70655, WO 01/41512, WO 02/02714, WO 02/15645, EP 1191613, EP 1191612, EP 1191614 and WO 05/033244. In general, phosphorescent complexes, as used in accordance with the prior art for phosphorescent OLEDs, are suitable here. If the OLED is to be produced from solution, the emitters should be correspondingly substituted in order that they likewise have sufficient solubility for processing from solution.

The mixture according to the invention comprises between 1 and 99% by weight, preferably between 3 and 95% by weight, particularly preferably between 5 and 50% by weight, in particular between 7 and 20% by weight, of the phosphorescent emitter, based on the mixture as a whole comprising emitter and matrix material. Correspondingly, the mixture according to the invention comprises between 99 and 1% by weight, preferably between 97 and 5% by weight, particularly preferably between 95 and 50% by weight, in particular between 93 and 80% by weight, of the matrix material according to the invention, based on the mixture as a whole comprising emitter and matrix material.

In a further preferred embodiment of the invention, the compound according to the invention is introduced in an interlayer between a fluorescent and a phosphorescent emitting layer, in particular between a blue-fluorescent and a green-, yellow-, orange- or red-phosphorescent layer. The use of compounds according to the invention in an interlayer of this type results in an increase in the efficiency of the OLED. If the compound of the formula (1) or of the formulae (4) to (10) is used in an interlayer of this type, it is preferably used as the pure substance.

Preference is furthermore given to an organic electroluminescent device, characterised in that one or more layers are coated by means of a sublimation process, in which the materials are vapour-deposited in vacuum sublimation units at a pressure below $10^{-5}$ mbar, preferably below $10^{-6}$ mbar, particularly preferably below $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar.

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Since the compounds according to the invention have high solubility in common organic solvents and good film-formation properties, they are also particularly suitable for processing from solution.

The compounds according to the invention have the following surprising advantages over the prior art on use in organic electroluminescent devices:
1. The charge balance of the OLEDs produced using the compounds according to the invention is leveled out better than with OLEDs in accordance with the prior art. This results in reduced operating voltages and thus higher efficiencies.
2. The lifetime of the devices is also improved.
3. The compounds according to the invention are readily soluble in common organic solvents. Furthermore, they have very good film-formation properties on processing from solution. This facilitates, in particular, solution-based processing of mixtures of the compounds according to the invention with soluble triplet emitters.
4. The use of the compounds according to the invention in an interlayer between a fluorescent and a phosphorescent emitting layer results in an increase in the efficiency of the organic electroluminescent device.

The present application text is directed to the use of the compounds according to the invention in relation to OLEDs and PLEDs and the corresponding displays. In spite of this restriction of the description, it is possible for the person skilled in the art, without further inventive step, also to employ the compounds according to the invention for further uses in other electronic devices, for example for organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photoreceptors.

The present invention likewise relates to the use of the compounds according to the invention in the corresponding devices and to these devices themselves.

The invention is explained in greater detail by the following examples, without wishing to restrict it thereby.

EXAMPLES

The following syntheses are carried out under a protective-gas atmosphere in dried solvents, unless indicated otherwise. The starting materials are purchased from ALDRICH [copper (I) cyanide, acetyl chloride, N-methylpyrrolidinone (NMP)].

2-Bromo-9,9'-spirobifluorene (J. Pei et al., *J. Org. Chem.* 2002, 67(14), 4924-4936) is prepared by the literature method. 2-Cyano-9,9'-spirobifluorene is synthesised as described in WO 04/093207.

Example 1

Synthesis of Compound M1 a) 2,7-Dibromo-2'-cyano-9,9-spirobifluorene

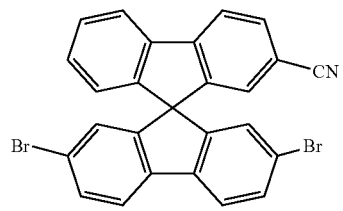 [SMILES: N#Cc1ccc2c(c1)C1(c3ccccc3-2)c2cc(Br)ccc2-c2ccc(Br)cc21]

80.0 g (234 mmol) of 2-cyano-9,9'-spirobifluorene are dissolved in 800 ml of dichloromethane. 69.0 g (5.62 mol) of $Na_2CO_3$ and 660 ml of water are added. 80 ml (0.97 mol) of bromine are added dropwise at 50° C., and the mixture is stirred at room temperature for 16 h. Saturated sodium sulfite solution is added to the reaction mixture at 0° C. with stirring until the mixture has become colourless. The organic phase is diluted with dichloromethane, washed with saturated sodium sulfite solution and water, dried over magnesium sulfate and evaporated to dryness. The crude product is recrystallised a number of times from toluene. Drying of the crystals in vacuo at 50° C. gives 76.5 g in 97% purity, corresponding to 65.4% of theory.

b) 2,7-Dibromo-9,9'-spirobifluoren-2'-yl 9,9'-spirobifluoren-2-yl ketone

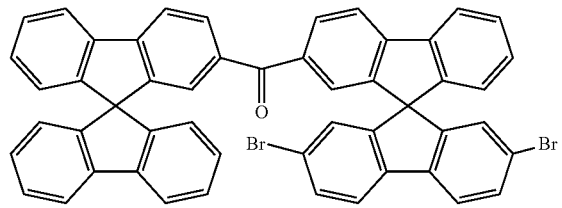 [SMILES: O=C(c1ccc2c(c1)C1(c3ccccc3-c3ccccc31)c1ccccc1-2)c1ccc2c(c1)C1(c3ccccc3-2)c2cc(Br)ccc2-c2ccc(Br)cc21]

The corresponding Grignard reagent is prepared from a solution of 40.0 g (101 mmol) of 2-bromo-9,9'-spirobifluorene and 1 ml of 1,2-dichloroethane in 30 ml of 1,2-dimethoxyethane and 300 ml of THF and 2.8 g (115 mmol) of magnesium at the boiling temperature. A solution of 50.6 g (101 mmol) of 2,7-dibromo-2'-cyano-9,9'-spirobifluorene in a mixture of 130 ml of THF and 130 ml of toluene is added dropwise to this Grignard solution at 0-5° C. over the course of 15 min. The mixture is subsequently heated under reflux for 16 h. After cooling, the reaction mixture is evaporated to dryness. The solid is taken up in 1100 ml of NMP and heated under reflux for 24 h with 40 ml of water and 0.05 ml of glacial acetic acid. A mixture of 600 ml of methanol and 600 ml of 1 N hydrochloric acid is added, and the precipitated solid is separated off by filtration and dried. The crude product is recrystallised a number of times from dioxane. The yield, with a purity>97% according to HPLC, is 41.5 g, corresponding to 50.2% of theory.

c) Synthesis of Compound M1

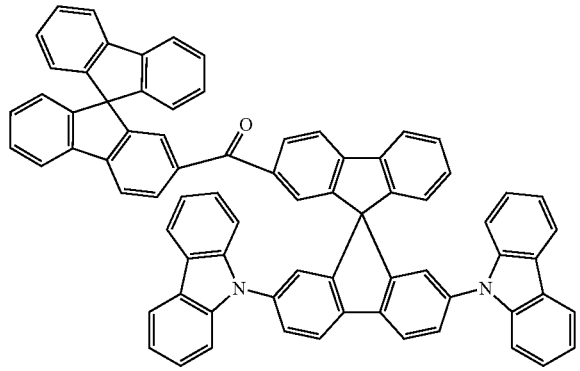 [SMILES: O=C(c1ccc2c(c1)C1(c3ccccc3-c3ccccc31)c1ccccc1-2)c1ccc2c(c1)C1(c3ccccc3-2)c2cc(-n3c4ccccc4c4ccccc43)ccc2-c2ccc(-n3c4ccccc4c4ccccc43)cc21]

39.0 g (223 mmol) of carbazole, 75.5 g (92.5 mmol) of 2,7-dibromo-9,9'-spirobifluoren-2'-yl 9,9'-spirobifluoren-2-yl ketone and 128.0 g (0.555 mol) of rubidium carbonate are suspended in 2500 ml of xylene. Tri-tert-butylphosphine and palladium acetate are subsequently added. The reaction mixture is stirred under reflux for 40 h. After cooling, the reaction mixture is washed a number of times with water and 1 N hydrochloric acid. The combined organic phases are dried over magnesium sulfate, and the solvent is removed on a rotary evaporator. The crude product is recrystallised a number of times from toluene. The yield, with a purity>99.99% according to HPLC, is 58.4 g, corresponding to 31.8% of theory $T_G$=213° C., $T_m$=350° C.

Example 2

Synthesis of Compound M2 a) Synthesis of tris-p-bromophenylphosphine oxide

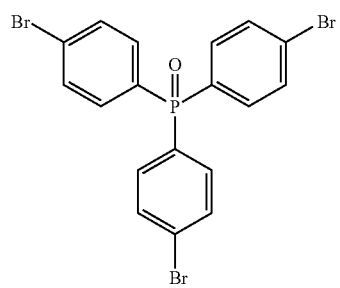 [SMILES: O=P(c1ccc(Br)cc1)(c1ccc(Br)cc1)c1ccc(Br)cc1]

The preparation of this compound is described in *Journal of Fluorine Chemistry* 2003, 124, 45-54.

b) Synthesis of tris-p-(9H-carbazolyl)phenylphosphine oxide (M2)

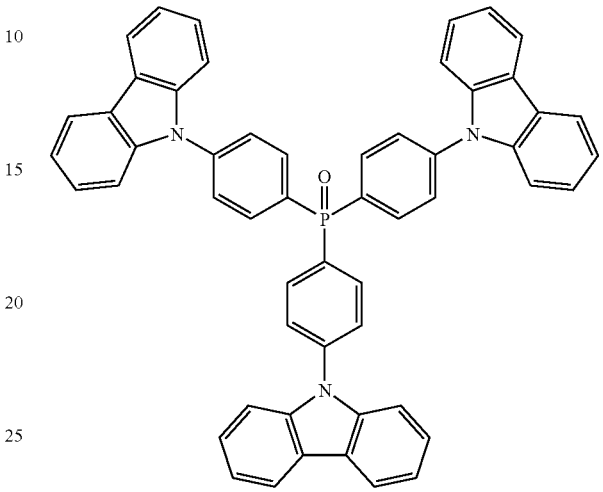

4.6 ml (18.7 mmol) of tri-ter-butylphosphine and, 5 min. later, 0.84 g (3.7 mmol) of palladium(II) acetate are added to a well-stirred, degassed suspension of 33.8 g (315 mmol) of tris-p-bromophenylphosphine oxide, 52.6 g (315 mmol) of carbazole and 140 g (1466 mmol) of $K_3PO_4$ in xylene, and the mixture is heated under reflux for 96 h. After cooling, the organic phase is separated off, washed three times with 200 ml of water and once with 300 ml of saturated, aqueous sodium chloride solution and subsequently dried over magnesium sulfate. After the drying agent has been filtered off, the organic phase is evaporated to dryness in vacuo in a rotary evaporator. The yellow residue obtained in this way is recrystallised from DMF. The deposited crystals are filtered off with suction, washed with a little MeOH and subsequently dried in vacuo; yield: 24.6 g, 48.4% of theory, purity: 99.9% according to HPLC. $T_G$=170° C., $T_m$=322° C.

Example 3

Synthesis of M3 a) Synthesis of 1,3-bis(4-bromobenzoyl)-5-tert-butylbenzene

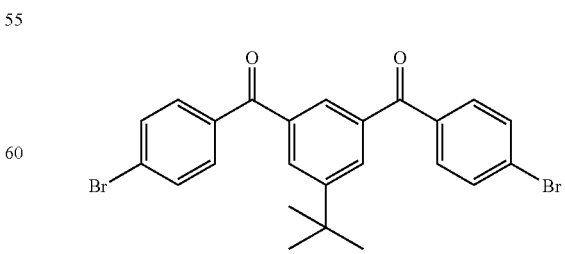

The preparation of this compound is described in *Macromolecules* 2004, 32, 8269-8277.

b) Synthesis of 1,3-bis[4-(diphenylamino)benzoyl-5-tert-butyl]benzene (M3)

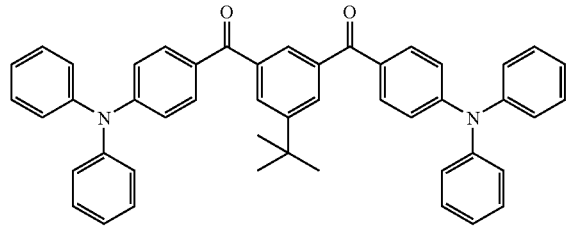 [SMILES: CC(C)(C)c1cc(C(=O)c2ccc(N(c3ccccc3)c3ccccc3)cc2)cc(C(=O)c2ccc(N(c3ccccc3)c3ccccc3)cc2)c1]

3.5 ml (14.9 mmol) of tri-tert-butylphosphine and, 5 min. later, 0.70 g (3.15 mmol) of palladium(II) acetate are added to a well-stirred, degassed suspension of 67 g (133 mmol) of 1,3-bis(4-bromobenzoyl-5-tert-butyl)benzene, 56.2 g (332.5 mmol) of diphenylamine and 36 g (373.6 mmol) of NaO$^t$Bu in toluene, and the mixture is heated under reflux for 8 h. After cooling, the organic phase is separated off, washed three times with 200 ml of water and once with 300 ml of saturated, aqueous sodium chloride solution and subsequently dried over magnesium sulfate. After the drying agent has been filtered off, the organic phase is evaporated to dryness in vacuo in a rotary evaporator. The yellow residue obtained in this way is recrystallised from DMF. The deposited crystals are filtered off with suction, washed with a little MeOH and subsequently dried in vacuo; yield: 43.1 g, 48% of theory; purity: 99.9% according to HPLC, $T_G$=96.1° C., $T_m$=196.8° C.

Example 4

Synthesis of M4 a) Synthesis of 1,3,5-tris(4-bromobenzoyl)benzene

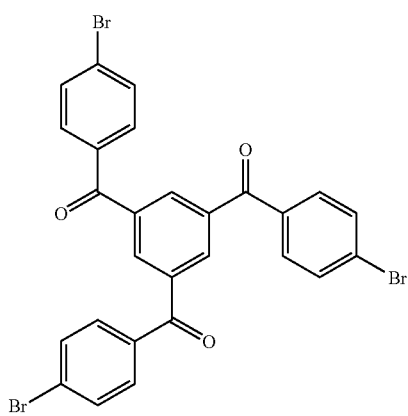 [SMILES: O=C(c1ccc(Br)cc1)c1cc(C(=O)c2ccc(Br)cc2)cc(C(=O)c2ccc(Br)cc2)c1]

The preparation of this compound is described in *Synthesis* 2003, 15, 2301-2303.

b) 1,3,5-Tris[4-(diphenylamino)benzoyl]benzene (M4)

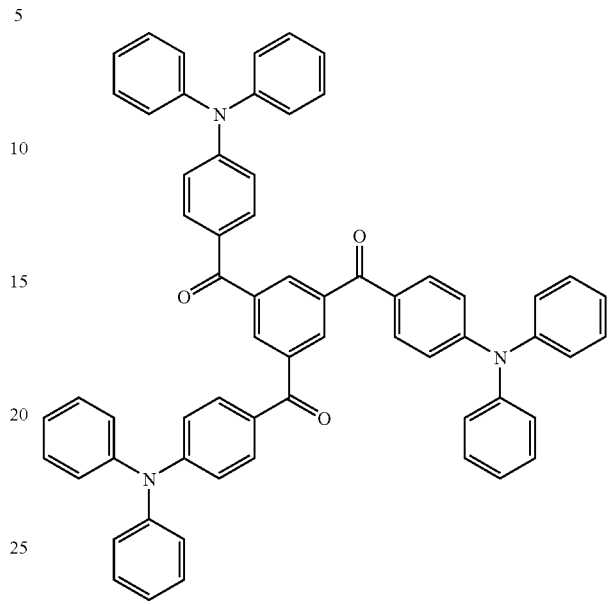

1.3 ml (5.38 mmol) of tri-tert-butylphosphine and, 5 min. later, 0.72 g (3.2 mmol) of palladium(II) acetate are added to a well-stirred, degassed suspension of 67 g (106.8 mmol) of 1,3,5-tris(4-bromobenzoyl)benzene, 68.7 g (405.9 mmol) of diphenylamine and 42.4 g (441.2 mmol) of NaO$^t$Bu in toluene, and the mixture is heated under reflux for 8 h. After cooling, the organic phase is separated off, washed three times with 200 ml of water and once with 300 ml of saturated, aqueous sodium chloride solution and subsequently dried over magnesium sulfate. After the drying agent has been filtered off, the organic phase is evaporated to dryness in vacuo in a rotary evaporator. The yellow residue obtained in this way is recrystallised from DMF. The deposited crystals are filtered off with suction, washed with a little MeOH and subsequently dried in vacuo; yield: 35 g, 37.4% of theory; purity: 99.9% according to HPLC. $T_G$=114° C., $T_m$=207° C.

Example 5

Production and Characterisation of Organic Electroluminescent Devices Comprising the Compounds According to the Invention Electroluminescent devices according to the invention can be produced as described, for example, in WO 05/003253. The results for various OLEDs are compared here. The basic structure, the materials used, the degree of doping and the layer thicknesses thereof are identical for better comparability. Exclusively the host in the emission layer is varied. The first example describes a comparative standard in accordance with the prior art, in which the emission layer consists of the host material BAlq and the guest material (dopant) Ir(piq)$_3$. Furthermore, an OLED having an emitter layer consisting of the host materials M1 to M4 and the guest material (dopant) Ir(piq)$_3$ is described. OLEDs having the following structure are produced analogously to the above-mentioned general process:

Hole-injection layer (HIL) 20 nm 2,2',7,7'-tetrakis(di-para-tolylamino)spiro-9,9'-bifluorene.
Hole-transport layer (HTL) 20 nm NPB (N-naphthyl-N-phenyl-4,4'-diaminobiphenyl).
Emission layer (EML) Host: BAlq (vapour-deposited; purchased from SynTec, bis(2-methyl-8-quinolinato)(para-phenylphenolato)aluminium(III)) as comparison or M1 to M4.
  Dopant: Ir(piq)$_3$ (10% doping, vapour-deposited; synthesised as described in WO 03/0068526).
Hole-blocking layer (HBL) 10 nm BAlq (purchased from SynTec, bis(2-methyl-8-quinolinato)(para-phenylphenolato)aluminium(III)).
Electron conductor (ETL) 20 nm AlQ$_3$ (purchased from SynTec, tris(quinolinato)aluminium(III)).
Cathode 1 nm LiF, 150 nm Al on top.

The structure of Ir(piq)$_3$ is shown below for reasons of clarity:

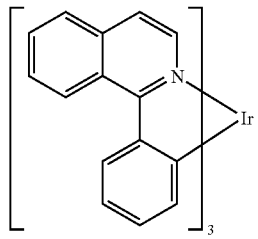

The still unoptimised OLEDs are characterised by standard methods, for this purpose, the electroluminescence spectra, the efficiency (measured in cd/A) as a function of the luminance, calculated from current-voltage-luminance characteristics (IUL characteristics), and the lifetime are determined.

Under the conditions described above, OLEDs produced using the standard host BAlq typically give a maximum efficiency of about 8.1 cd/A at CIE colour coordinates of: x=0.68, y=0.32. For the reference luminance of 1000 cd/m$^2$, voltages of 7.2 V are required. The lifetime is about 6300 h at an initial luminance of 1000 cd/m$^2$ (see Table 1). By contrast, OLEDs produced using hosts M1 to M4 according to the invention, with an otherwise identical structure, exhibit maximum efficiencies of up to 8.9 cd/A at CIE colour coordinates of: x=0.68, y=0.32, with the requisite voltage for the reference luminance of 1000 cd/m$^2$ being 5.6 V (see Table 1). The lifetime of 7900 h at an initial luminance of 1000 cd/m$^2$ is longer than with the reference material BAlq (see Table 1).

The invention claimed is:
1. A compound of formulae (6), (7), (8), (9), or (10)

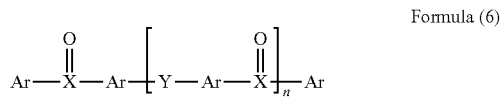

Formula (6)

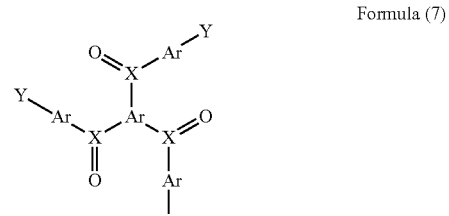

Formula (7)

Formula (8)

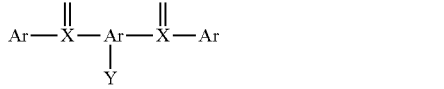

Formula (9)

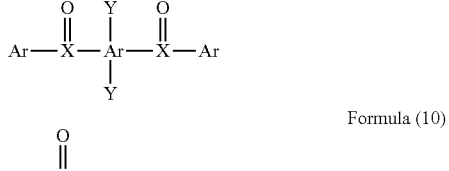

Formula (10)

wherein
X is, identically or differently on each occurrence, C, P(Ar), or P(Ar-Y);
Ar is, identically or differently on each occurrence an aromatic or heteroaromatic ring system having 5 to 60 aromatic ring atoms optionally substituted by one or more radicals R$^1$, wherein Ar contains phenyl and/or naphthyl groups, but no larger condensed aromatic systems;
R$^1$ is, identically or differently on each occurrence, H, F, N(Ar$^1$)$_2$, CN, NO$_2$, Si(R$^2$)$_3$, B(OR$^2$)$_2$, C(=O)Ar$^1$, P(=O)(Ar$^1$)$_2$, CR$^2$=CR$^2$(Ar$^1$), a straight-chain alkyl, alkoxy or thioalkoxy group having 1 to 40 C atoms optionally substituted by one or more radicals R$^2$, a branched or cyclic alkyl, alkoxy or thioalkoxy group having 3 to 40 C atoms optionally substituted by one or more radicals R$^2$, wherein one or more non-adjacent CH$_2$ groups of said straight-chain alkyl, alkoxy, or thio-

TABLE 1

Device results with host materials according to the invention with Ir(piq)$_3$ as dopant

| Experiment | EML | Max. efficiency [cd/A] | Voltage [V] at 1000 cd/m$^2$ | CIE (x, y) | Lifetime [h] initial luminance 1000 [cd/m$^2$] |
|---|---|---|---|---|---|
| Example 6 (comparison) | BAlq: 10% Ir(piq)$_3$ (30 nm) | 8.1 | 7.2 | 0.68/0.32 | 6300 |
| Example 7 | M1: 10% Ir(piq)$_3$ (30 nm) | 8.5 | 6.0 | 0.68/0.32 | 7500 |
| Example 8 | M2: 10% Ir(piq)$_3$ (30 nm) | 8.5 | 5.8 | 0.68/0.32 | 7900 |
| Example 9 | M3: 10% Ir(piq)$_3$ (30 nm) | 8.7 | 5.6 | 0.68/0.32 | 8200 |
| Example 10 | M4: 10% Ir(piq)$_3$ (30 nm) | 8.9 | 5.7 | 0.68/0.32 | 7800 | alkoxy group or said branched or cyclic alkyl, alkoxy, or thioalkoxy group is optionally replaced by $R^2C=CR^2$, $Si(R^2)_2$, $C=O$, $P(=O)(R^2)$, SO, $SO_2$, $NR^2$, O, S, or $CONR^2$ and wherein one or more H atoms of said straight-chain alkyl, alkoxy, or thioalkoxy group or said branched or cyclic alkyl, alkoxy, or thioalkoxy group is optionally replaced by F, an aromatic or heteroaromatic ring system having 5 to 60 aromatic ring atoms, which is optionally substituted by one or more radicals $R^2$, or an aryloxy or heteroaryloxy group having 5 to 60 aromatic ring atoms, which is optionally substituted by one or more radicals $R^2$, or a combination of these systems;

$Ar^1$ is, identically or differently on each occurrence, an aromatic or heteroaromatic ring system having 5 to 60 aromatic ring atoms, which is optionally substituted by one or more radicals $R^2$;

$R^2$ is, identically or differently on each occurrence, H, F, or an aliphatic, aromatic, and/or heteroaromatic hydrocarbon radical having 1 to 20 C atoms, wherein H atoms are optionally replaced by F; and wherein two or more substituents $R^2$ optionally define a mono- or polycyclic aliphatic or aromatic ring system with one another;

Y is, identically or differently on each occurrence, in formulae (7), (8) and (9), a group of formula (2) or formula (3), and in formulae (6) and (10), a group of formula (2)

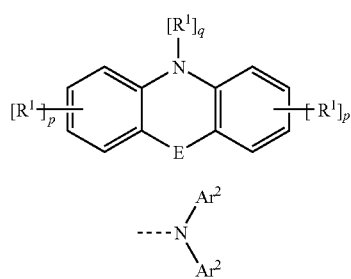

Formula (2)

Formula (3)

wherein said group of formula (2) is linked to Ar via any position and said group of formula (3) is linked to Ar via N, wherein $R^1$ is as defined above and:

E is O, S, $N(R^1)$, $P(R^1)$, $P(=O)R^1$, $C(R^1)_2$, $Si(R^1)_2$, or a single bond;

$Ar^2$ is, identically or differently on each occurrence, an aryl or heteroaryl group having 5 to 20 aromatic ring atoms or a triarylamine group having 15 to 30 aromatic ring atoms, each of which is optionally substituted by one or more radicals $R^1$, with the proviso that at least one substituent $R^1$ is an alkyl or silyl group and is present on at least one $Ar^2$ group;

p is, identically or differently on each occurrence, 0, 1, 2, 3 or, 4;

q is 0 or 1, wherein q is 0 if said group of formula (2) is bonded to Ar via the nitrogen and q is 1 if said group of formula (2) is bonded to Ar via an atom other than the nitrogen;

with the proviso that the group Ar which is bonded to X and to Y is not continuously conjugated if said compound has precisely one carbonyl function; and n is, identically or differently on each occurrence, is 1, 2, 3, 4, or 5.

2. The compound of claim 1, wherein said compound contains at least two X=O groups and/or at least two Y groups.

3. The compound of claim 1, wherein the ratio of X=O groups to Y groups is in the range of from 1:10 to 10:1.

4. The compound of claim 1, wherein the Ar group simultaneously bonded to X and to Y is not continuously conjugated.

5. The compound of claim 1, wherein the groups Ar simultaneously bonded to X and to Y are selected from the group consisting of units of formulae (11), (12), (13), (14), (15), (16), and (17):

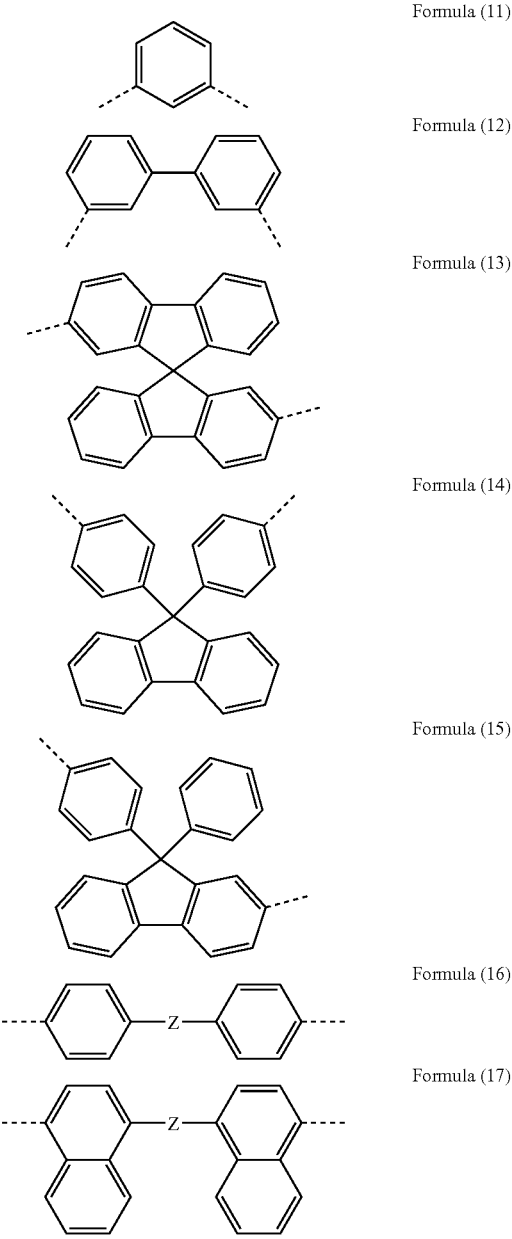

wherein
in each case the dashed line is the bond to X and to Y and wherein said units of formulae (11), (12), (13), (14), (15), (16), and (17) are optionally substituted by one or more radicals $R^1$;

Z is, identically or differently on each occurrence, —[C$(R^1)_2]_k$—, $Si(R^1)_2$, O, or S; and k is 1, 2, 3, 4, 5, or 6.

6. The compound of claim 1, wherein Y is, identically or differently on each occurrence, a group of formula (2a) or (3a)

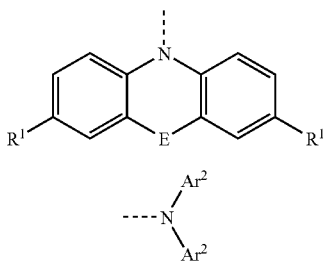

Formula (2a)

Formula (3a)

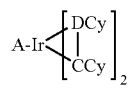

Formula (18)

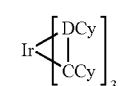

Formula (19)

Formula (20)

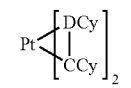

Formula (21)

wherein
said group of formula (2a) or (3a) is linked to Ar via the nitrogen;
E is a single bond, O, S, or $N(R^1)$;
$Ar^2$ is, identically or differently on each occurrence, an aryl or heteroaryl group having 5 to 10 aromatic ring atoms or a triarylamine group having 18 to 24 aromatic ring atoms, each of which is optionally substituted by one or more radicals $R^1$, with the proviso that at least one substituent $R^1$ is an alkyl or silyl group and is present on at least one $Ar^2$ group.

7. The compound of claim 1, wherein $R^1$ is, identically or differently on each occurrence, H, F, $N(Ar^1)_2$, $P(=O)(Ar^1)_2$, $C(=O)Ar^1$, $CR^2=CR^2Ar^1$, a straight-chain alkyl group having 1 to 5 C atoms, a branched alkyl group having 3 to 5 C atoms, wherein one or more non-adjacent $CH_2$ groups of said straight-chain alkyl group or said branched alkyl group is optionally replaced by $-R^2C=CR^2-$ or $-O-$ and one or more H atoms of said straight-chain alkyl group or said branched alkyl group is optionally replaced by F, an aryl group having 6 to 16 C atoms, a heteroaryl group having 2 to 16 C atoms, or a spirobifluorenyl group, each of which is optionally substituted by one or more radicals $R^2$, or a combination of two or three of these systems.

8. The compound of claim 1, wherein all X are identical.
9. The compound of claim 1, wherein all Y are identical.
10. The compound of claim 1, wherein all $R^1$ are identical.
11. The compound of claim 8, wherein all Y are identical and all $R^1$ are identical.
12. A process for preparing the compound of claim 1, comprising synthesizing said compound by Hartwig-Buchwald coupling of an aromatic ketone substituted by one or more halogens or one or more groups $OSO_2R^2$ to a diarylamino group, wherein the two aryl groups are optionally bridged by a group E.
13. A device comprising an anode, a cathode, and an organic layer comprising a compound of claim 1.
14. The device of claim 13, wherein said device is an organic electroluminescent device.
15. The device of claim 13, wherein said organic layer is in an interlayer between a fluorescent and a phosphorescent emitting layer.
16. The device of claim 13, wherein said organic layer is an emitting layer and said compound is a matrix for a phosphorescent dopant.
17. The device of claim 16, wherein said phosphorescent dopant is a compound of formulae (18), (19), (20), and (21)

or mixtures thereof, and
wherein
DCy is, identically or differently on each occurrence, a cyclic group which contains at least one donor atom via which the cyclic group is bonded to the metal and is optionally substituted with one or more substituents $R^1$;
CCy is, identically or differently on each occurrence, a cyclic group which contains a carbon atom via which the cyclic group is bonded to the metal and is optionally substituted with one or more substituents $R^1$;
wherein DCy and CCy are connected to one another via a covalent bond;
A is, identically or differently on each occurrence, a monoanionic, bidentate chelating ligand; and
$R^1$ is, identically or differently on each occurrence, H, F, Cl, Br, I, $N(Ar^1)_2$, CN, $NO_2$, $Si(R^2)_3$, $B(OR^2)_2$, $C(=O)Ar^1$, $P(=O)(Ar^1)_2$, $S(=O)Ar^1$, $S(=O)_2Ar^1$, $CR^2=CR^2(Ar^1)$, tosylate, triflate, $OSO_2R^2$, a straight-chain alkyl, alkoxy or thioalkoxy group having 1 to 40 C atoms optionally substituted by one or more radicals $R^2$, a branched or cyclic alkyl, alkoxy or thioalkoxy group having 3 to 40 C atoms optionally substituted by one or more radicals $R^2$, wherein one or more non-adjacent $CH_2$ groups of said straight-chain alkyl, alkoxy, or thioalkoxy group or said branched or cyclic alkyl, alkoxy, or thioalkoxy group is optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S, or $CONR^2$ and wherein one or more H atoms of said straight-chain alkyl, alkoxy, or thioalkoxy group or said branched or cyclic alkyl, alkoxy, or thioalkoxy group is optionally replaced by F, Cl, Br, I, CN, or $NO_2$, an aromatic or heteroaromatic ring system having 5 to 60 aromatic ring atoms, which is optionally substituted by one or more radicals $R^2$, or an aryloxy or heteroaryloxy group having 5 to 60 aromatic ring atoms, which is optionally substituted by one or more radicals $R^2$, or a combination of these systems; and wherein two or more substituents $R^1$ optionally define a mono- or polycyclic aliphatic or aromatic ring system with one another.

18. The device of claim 17, wherein said at least one donor atom in DCy is nitrogen or phosphorus and A is a diketonate ligand.

* * * * *